(12) United States Patent
Sims et al.

(10) Patent No.: US 7,270,817 B2
(45) Date of Patent: Sep. 18, 2007

(54) ACPL ANTIBODIES AND METHODS OF USE THEREOF

(75) Inventors: John E. Sims, Seattle, WA (US); Teresa L. Born, Seattle, WA (US)

(73) Assignee: Immunex Corporation, Thousand Oaks, CA (US)

(*) Notice: Subject to any disclaimer, the term of this patent is extended or adjusted under 35 U.S.C. 154(b) by 392 days.

(21) Appl. No.: 10/774,192

(22) Filed: Feb. 6, 2004

(65) Prior Publication Data

US 2004/0138421 A1 Jul. 15, 2004

Related U.S. Application Data

(60) Continuation of application No. 10/212,356, filed on Aug. 2, 2002, now Pat. No. 6,692,740, which is a division of application No. 09/616,530, filed on Jul. 14, 2000, now Pat. No. 6,664,077, which is a continuation of application No. PCT/US99/01420, filed on Jan. 22, 1999.

(60) Provisional application No. 60/078,835, filed on Mar. 20, 1998, provisional application No. 60/072,301, filed on Jan. 23, 1998.

(51) Int. Cl.
*A61K 39/395* (2006.01)
*C07K 16/28* (2006.01)

(52) U.S. Cl. .............. 424/143.1; 424/130.1; 424/133.1; 424/139.1; 530/387.1; 530/387.3; 530/387.9; 530/388.22

(58) Field of Classification Search .............. None
See application file for complete search history.

(56) References Cited

U.S. PATENT DOCUMENTS 6,326,472 B1 12/2001 Timans et al.

FOREIGN PATENT DOCUMENTS

EP 0 464 533 A1 6/1991
WO WO99/19480 10/1998

OTHER PUBLICATIONS

Bacher et al. (2004). The NF-KB pathway as a potential target for autoimmune disease therapy. Current Pharmaceutical Design. 10:2827-2837.*
Lejeune et al. (2002). The interleukin-22 (IL-22) activates the JAK/STAT, ERK, JNK, and p38 MAP kinase pathways in a rat hepatoma cell line. The Journal of Biological Chemistry. 37:33676-33682.*

Wullaert et al. (2006). Mechanisms of crosstalk between TNF-induced NF-KB and JNK activation in hepatocytes. Biochemical Pharmacology. 72:1090-1101.*
Li et al. (2001). IL-1-induced NFKB and c-Jun N-terminal kinase (JNK) activation diverge at IL-1 receptor-associated kinase (IRAK). Proc. Natl. Acad. Sci. USA 98(8):4461-4465.*
Debets et al. (2000). IL-18 receptors, their role in ligand binding and function: anti-IL-1RAcPL antibody, a potent antagonist of IL-18. The Journal of Immunology. 165:4950-4956.*
Gillespie et al. (1998). Interleukin-18: perspectives on the newest interleukin. Cytokine and Growth Factor Reviews. 9(2):109-116.*
Adachi et al. (1998). Targeted disruption of the MyD88 gene results in loss of IL-1- and IL-18-mediated function. Immunity. 9:143-150.*
Bonnert, T. P. et al., "The cloning and characterization of human MyD88: a member of an IL-1 receptor related family," *FEBS Letters*, 402:81-84, 1997.
Born T. L. et al., "Cloning of a novel receptor subunit, AcPL, required for Interleukin-18 signaling," *J. Biol. Chem.*, 273(45) 29445-29450, 1998.
Greenfeder S. A. et al., "Molecular cloning and characterization of a second subunit of the Interleukin 1 receptor complex," *J. Biol. Chem.*, 270(23):13757-13765, 1995.
Lovenberg, T. W. et al., "Cloning of a cDNA encdoding a novel interleukin-1 receptor related protein (IL1R-rp2)," *J. Neuroimmunol.*, 70:113-122, 1996.
Parnet P. et al., "IL-1Rrp is a novel receptor-like molecule similar to the type I Interleukin-1 receptor and its homologues T1/ST2 and IL-1R AcP," *J. Biol. Chem.*, 271(8):3967-3970, 1996.
Rock, F. L. et al., "A family of human receptors structurally related to Drosophila Toll," *Proc. Natl. Acad. Sci. USA*, 95:588-593, 1998.
Thomassen, E. et al., "Binding of interleukin-18 to the interleukin-1 receptor homologous receptor IL-1Rrp1 leads to activation of signaling pathways similar to those used by interleukin-1," *J. Interferon Cytokine Res.*, 18:1077-1088, 1998.
Torigoe K. et al., "Purification and characterization of the human Interleukin-18 receptor," *J. Biol. Chem.*, 272(41):25737-25742, 1997.

* cited by examiner

*Primary Examiner*—Christine J. Saoud
*Assistant Examiner*—Jon M Lockard
(74) *Attorney, Agent, or Firm*—Thomas J. Wrona; Janis C. Henry

(57) ABSTRACT

The invention is directed to purified and isolated novel ACPL polypeptides, the nucleic acids encoding such polypeptides, processes for production of recombinant forms of such polypeptides, antibodies generated against these polypeptides, fragmented peptides derived from these polypeptides, and the uses of the above.

8 Claims, No Drawings

ACPL ANTIBODIES AND METHODS OF USE THEREOF

CROSS-REFERENCE TO RELATED APPLICATIONS

This application is a continuation of U.S. patent application Ser. No. 10/212,356, filed Aug. 2, 2002, now U.S. Pat. No. 6,692,740, which is a divisional of U.S. patent application Ser. No. 09/616,530, filed on Jul. 14, 2000, now U.S. Pat. No. 6,664,077, which is a continuation of international application PCT/US99/01420, filed on Jan. 22, 1999, which claims the benefit under 35 U.S.C. § 119(e) of U.S. Provisional Application Ser. No. 60/072,301, filed Jan. 23, 1998, and U.S. Provisional Application Ser. No. 60/078,835, filed March 20, 1998, all of which are incorporated by reference herein.

BACKGROUND OF THE INVENTION

1. Field of the Invention

The invention is directed to purified and isolated ACPL polypeptides, the nucleic acids encoding such polypeptides, processes for production of recombinant forms of such polypeptides, antibodies generated against these polypeptides, fragmented peptides derived from these polypeptides, the use of such polypeptides and fragmented peptides as molecular weight markers, the use of such polypeptides and fragmented peptides as controls for peptide fragmentation, and kits comprising these reagents. The invention is further directed to the use of ACPL polypeptides, the nucleic acids encoding such polypeptides, and antibodies generated against these polypeptides in the study of cell signaling in response to IL-18 stimulation, and inducible protein expression systems based on the involvement of ACPL polypeptides in cell signaling.

2. Description of Related Art

The IL-1 type I receptor (IL-1R) mediates the biological effects of IL-1. Activities attributed to IL-1α and IL-1β include induction of inflammatory cytokines and other inflammatory responses including prostaglandins, metalloproteinases, adhesion molecules, acute phase proteins, hematopoiesis, fever, bone resorption, and Th2 cell growth and differentiation.

IL-1 has been implicated in chronic inflammatory diseases, such as rheumatoid arthritis and inflammatory bowel disease. There is increasing evidence that IL-1 plays a role in osteoporosis. All of these activities are initiated by the signaling function of the cytoplasmic portion of the type I IL-1R. IL-1ra inhibits the activities of IL-1 by binding to the type I IL-1 receptor, thereby blocking access to IL-1α and IL-1β while eliciting no biological response of its own.

IL-18 is a homolog of IL-1α and IL-1β, and may mediate its activities via a receptor homologous to IL-1R, IL-1 receptor related protein 1 (IL-1RrpI)(See Parnet et al., *J. Biol. Chem* 271:3967, 1996, and Torigoe et al., *J. Biol. Chem* 272:25737, 1997). IL-18 acts as a stimulator of Th1 cell growth and differentiation, and is a potent inducer of interferon production from Th1 cells. IL-18 enhances NK cell killing activity and has been implicated in septic shock, liver destruction, and diabetes. Furthermore IL-18 exhibits in vivo antitumor effects in mice, which are immunologically mediated (Mieallef et al., *Cancer Immunol. Immunother.* 43:361, 1997).

The discovery and identification of proteins is at the forefront of modern molecular biology and biochemistry.

The identification of the primary structure, or sequence, of a sample protein is the culmination of an arduous process of experimentation. In order to identify an unknown sample protein, the investigator can rely upon comparison of the unknown sample protein to known peptides using a variety of techniques known to those skilled in the art. For instance, proteins are routinely analyzed using techniques such as electrophoresis, sedimentation, chromatography, and mass spectrometry.

Comparison of an unknown protein sample to polypeptides of known molecular weight allows a determination of the apparent molecular weight of the unknown protein sample (T. D. Brock and M. T. Madigan, *Biology of Microorganisms* 76-77 (Prentice Hall, 6d ed. 1991)). Protein molecular weight standards are commercially available to assist in the estimation of molecular weights of unknown protein samples (New England Biolabs Inc. Catalog: 130-131, 1995; J. L. Hartley, U.S. Pat. No. 5,449,758). However, the molecular weight standards may not correspond closely enough in size to the unknown sample protein to allow an accurate estimation of apparent molecular weight.

The difficulty in estimation of molecular weight is compounded in the case of proteins that are subjected to fragmentation by chemical or enzymatic means (A. L. Lehninger, *Biochemistry* 106-108 (Worth Books, 2d ed. 1981)). Chemical fragmentation can be achieved by incubation of a protein with a chemical, such as cyanogen bromide, which leads to cleavage of the peptide bond on the carboxyl side of methionine residues (E. Gross, *Methods in Enz.* 11:238-255, 1967). Enzymatic fragmentation of a protein can be achieved by incubation of a protein with a protease that cleaves at multiple amino acid residues (D. W. Cleveland et al., *J. Biol. Chem.* 252:1102-1106, 1977). Enzymatic fragmentation of a protein can also be achieved by incubation of a protein with a protease, such as Achromobacter protease I (F. Sakiyama and A. Nakata, U.S. Pat. No. 5,248,599; T. Masaki et al., *Biochim. Biophys. Acta* 660:44-50, 1981; T. Masaki et al., *Biochim. Biophys. Acta* 660:51-55, 1981), which leads to cleavage of the peptide bond on the carboxyl side of lysine residues. The molecular weights of the fragmented peptides can cover a large range of molecular weights and the peptides can be numerous. Variations in the degree of fragmentation can also be accomplished (D. W. Cleveland et al., *J. Biol. Chem.* 252:1102-1106, 1977).

The unique nature of the composition of a protein with regard to its specific amino acid constituents results in a unique positioning of cleavage sites within the protein. Specific fragmentation of a protein by chemical or enzymatic cleavage results in a unique "peptide fingerprint" (D. W. Cleveland et al., *J. Biol. Chem.* 252:1102-1106, 1977; M. Brown et al., *J. Gen. Virol.* 50:309-316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms* 76-77 (Prentice Hall, 6d ed. 1991)).

When a peptide fingerprint of an unknown protein is obtained, this can be compared to a database of known proteins to assist in the identification of the unknown protein (W. J. Henzel et al., *Proc. Natl. Acad. Sci. USA* 90:5011-5015, 1993; B. Thiede et al., *Electrophoresis* 1996, 17:588-599, 1996). A variety of computer software programs are accessible via the Internet to the skilled artisan for the facilitation of such comparisons, such as Multildent, PeptideSearch, and ProFound. These programs allow the user to specify the cleavage agent and the molecular weights of the fragmented peptides within a designated tolerance. The programs compare these molecular weights to protein databases to assist in the elucidation of the identity of the sample protein. Accurate information concerning the number of fragmented peptides and the precise molecular weight of those peptides is required for accurate identification. Therefore, increasing the accuracy in the determination of the number of fragmented peptides and the precise molecular weight of those peptides should result in enhanced success in the identification of unknown proteins.

Fragmentation of proteins is further employed for the production of fragments for amino acid composition analysis and protein sequencing (P. Matsudiara, *J. Biol. Chem.* 262:10035-10038, 1987; C. Eckerskorn et al., *Electrophoresis* 1988, 9:830-838, 1988), particularly the production of fragments from proteins with a "blocked" N-terminus. In addition, fragmentation of proteins can be used in the preparation of peptides for mass spectrometry (W. J. Henzel et al., *Proc. Natl. Acad. Sci. USA* 90:5011-5015, 1993; B. Thiede et al., *Electrophoresis* 1996, 17:588-599, 1996), for immunization, for affinity selection (R. A. Brown, U.S. Pat. No. 5,151,412), for determination of modification sites (e.g. phosphorylation), for generation of active biological compounds (T. D. Brock and M. T. Madigan, *Biology of Microorganisms* 300-301 (Prentice Hall, 6d ed: 1991)), and for differentiation of homologous proteins (M. Brown et al., *J. Gen. Virol.* 50:309-316, 1980).

In view of the continuing interest in protein research and the elucidation of protein structure and properties, there exists a need in the art for polypeptides suitable for use in peptide fragmentation studies and in molecular weight measurements.

SUMMARY OF THE INVENTION

The invention encompasses isolated nucleic acid molecules comprising the DNA sequences of SEQ ID NO:1 SEQ ID NO:3, the coding region of SEQ ID NO:6, and isolated nucleic acid molecules encoding the amino acid sequence of SEQ ID NO:2 and SEQ ID NO:7. The invention also encompasses nucleic acid molecules complementary to these sequences. As such, the invention includes double-stranded nucleic acid molecules comprising the DNA sequences of SEQ ID NO: 1 and the coding region of SEQ ID NO:6, and isolated nucleic acid molecules encoding the amino acid sequences of SEQ ID NO:2 and SEQ ID NO:7. Both single-stranded and double-stranded RNA and DNA ACPL nucleic acid molecules are encompassed by the invention. These molecules can be used to detect both single-stranded and double-stranded RNA and DNA variants of ACPL encompassed by the invention. A double-stranded DNA probe allows the detection of nucleic acid molecules equivalent to either strand of the nucleic acid molecule. Isolated nucleic acid molecules that hybridize to a denatured, double-stranded DNA comprising the DNA sequence of SEQ ID NO: 1 or SEQ ID NO:6, or an isolated nucleic acid molecule encoding the amino acid sequence of SEQ ID NO:2 or SEQ ID NO:7 under conditions of moderate stringency in 50% formamide and 6×SSC, at 42° C. with washing conditions of 60° C., 0.5×SSC, 0.1% SDS are encompassed by the invention.

The invention further encompasses isolated nucleic acid molecules derived by in vitro mutagenesis from SEQ ID NO:1 or SEQ ID NO:6. In vitro mutagenesis would include numerous techniques known in the art including, but not limited to, site-directed mutagenesis, random mutagenesis, and in vitro nucleic acid synthesis. The invention also encompasses isolated nucleic acid molecules degenerate from SEQ ID NO: 1 and SEQ ID NO:6, as a result of the genetic code; isolated nucleic acid molecules that are allelic variants of human ACPL DNA, or a species homolog of ACPL DNA. The invention also encompasses recombinant vectors that direct the expression of these nucleic acid molecules and host cells transformed or transfected with these vectors.

The invention also encompasses isolated polypeptides encoded by these nucleic acid molecules, including isolated polypeptides having a molecular weight of approximately 70 kD as determined by SDS-PAGE and isolated polypeptides in non-glycosylated form. Isolated polyclonal or monoclonal antibodies that bind to these polypeptides are encompassed by the invention. The invention further encompasses methods for the production of ACPL polypeptides including culturing a host cell under conditions promoting expression and recovering the polypeptide from the culture medium. Especially, the expression of ACPL polypeptides in bacteria, yeast, plant, and animal cells is encompassed by the invention.

In addition, assays utilizing ACPL polypeptides to screen for potential inhibitors of activity associated with ACPL polypeptide counter-structure molecules or ACPL binding proteins, and methods of using ACPL polypeptides as therapeutic agents for the treatment of diseases mediated by ACPL polypeptide counter-structure molecules or binding proteins are encompassed by the invention. Further, methods of using ACPL polypeptides in the design of inhibitors thereof are also an aspect of the invention.

The invention further encompasses the fragmented peptides produced from ACPL polypeptides by chemical or enzymatic treatment. In addition, forms of ACPL polypeptide molecular weight markers and fragmented peptides thereof, wherein at least one of the sites necessary for fragmentation by chemical or enzymatic means has been mutated, are an aspect of the invention.

The invention also encompasses a method for the visualization of ACPL polypeptide molecular weight markers and fragmented peptides thereof using electrophoresis. The invention further includes a method for using ACPL polypeptide molecular weight markers and fragmented peptides thereof as molecular weight markers that allow the estimation of the molecular weight of a protein or a fragmented protein sample. The invention further encompasses methods for using ACPL polypeptides and fragmented peptides thereof as markers, which aid in the determination of the isoelectric point of a sample protein. The invention also encompasses methods for using ACPL polypeptides and fragmented peptides thereof as controls for establishing the extent of fragmentation of a protein sample.

Further encompassed by this invention are kits to aid the determination of molecular weights of a sample protein utilizing ACPL polypeptide molecular weight markers, fragmented peptides thereof, and forms of ACPL polypeptide molecular weight markers, wherein at least one of the sites necessary for fragmentation by chemical or enzymatic means has been mutated.

Also encompassed by this invention are processes associated with inducible protein expression systems based upon ACPL-dependent induction. Such systems can include, but are not limited to, ACPL-dependent induction of NFkB-mediated signaling in response to IL-18 stimulation and Ap-1-mediated signaling in response to IL-18 stimulation. Further encompassed within the present invention are processes that are associated with responses to the IL-18 induction of the MAP kinase family, kinases JNK and p38.

DETAILED DESCRIPTION OF THE INVENTION cDNAs encoding mouse and human ACPL polypeptides have been isolated and are disclosed in SEQ ID NO: 1, SEQ ID NO:3, SEQ ID NO:4 and SEQ ID NO:6. This discovery of the cDNAs encoding ACPL polypeptides enables construction of expression vectors comprising nucleic acid sequences encoding ACPL polypeptides and ACPL polypeptide fragments; construction of host cells transfected or transformed with the expression vectors; construction of biologically active ACPL polypeptides and ACPL molecular weight markers as isolated and purified proteins; and the preparation of antibodies immunoreactive with ACPL polypeptides.

ACPL nucleotides and polypeptides were obtained as follows. The IMAGE clone of EST sequence AA203986, which was derived from mouse thymus, was obtained and sequenced. This sequence information was used to screen a cDNA library from mouse T cells (EL4), and a full-length murine clone of ACPL DNA was isolated and sequenced. The ACPL sequence represents sequence from at least three independent isolates over the entire open reading frame. The sequence of the coding region of mouse ACPL DNA is given in SEQ ID NO: 1. The amino acid sequence encoded by SEQ ID NO: 1 is presented in SEQ ID NO:2. The mouse ACPL encoded by SEQ ID NO:1 includes an extracellular domain of 356 amino acids (residues 1-356 from N- to C-terminus of SEQ ID NO:2) that includes a signal peptide of 14 amino acids (residues 1-14 of SEQ ID NO:2); a transmembrane region of 24 amino acids (residues 357-380 of SEQ ID NO:2) and a cytoplasmic domain of amino acids (residues 381-614 of SEQ ID NO:2).

The sequence of this clone shows similarity to the sequence of members of the IL-1 receptor family thereby demonstrating that the mouse ACPL DNA (SEQ ID NO: 1) encodes a receptor (SEQ ID NO:2) that is a member of the IL-1 receptor family.

A clone derived from a human NK cell library, QQ1352, was identified as a human homolog of mouse ACPL DNA. Clone QQ1352 represents a partially spliced mRNA clone, and part of this sequence is identical to the sequence of an exon found within a genomic DNA clone from a BAC, that was deposited in Genbank under accession number B64403. Furthermore, this sequence (nucleotides 179-244 of SEQ ID NO:5) corresponds in position to exon 7 of the human type I IL-1R, and indicates an involvement of ACPL polypeptide in mediating inflamatory responses.

The amino acid sequence encoded by the QQ1352 clone was compared to the mouse ACPL polypeptide sequence. Bestfit comparisons were performed with mouse ACPL polypeptide sequence with translations in 3 different frames of the QQ1352 sequence, beginning at nucleotide 522. It is apparent from these alignments that there are at least two frameshifts leading to significant homology between the mouse and human sequences in all three frames depending on the position in the sequence, demonstrating the QQ1352 contains a portion of human ACPL.

To obtain full length human ACPL, the human cDNA clone, QQ1352, was used to to probe clones from PBL, PBT and NK cDNA libraries. The region of clone QQ1352 used as a probe was homologous to murine ACPL nucleotides 1196 through 1753. A full-length clone was not obtained from any of the libraries, so vector-anchored PCR was carried out in each of the libraries to obtain the 5' end of the open reading frame. The full DNA sequence of human ACPL is disclosed in SEQ ID NO:6. The amino acid sequence encoded by SEQ ID NO:6 is presented in SEQ ID NO:7. The ACPL encoded by SEQ ID NO:6 includes an extracellular domain of 356 amino acids (residues 1-356 from N- to C-terminus of SEQ ID NO:7) that includes a signal peptide of 14 amino acids (residues 1-14 of SEQ ID NO:7); a transmembrane region of 25 amino acids (residues 357-381 of SEQ ID NO:7) and a cytoplasmic domain of amino acids (residues 382-599 of SEQ ID NO:7).

The coexpression of ACPL and IL-1Rrp1 results in a dramatic enhancement of NFkB activity in cells stimulated with IL-18. In contrast, the expression of ACPL or IL-1Rrp1 alone does not result in IL-18 responsiveness. Therefore, ACPL plays a role in mediating IL-18 responses, and can be a component of the IL-18 receptor complex. In addition, a receptor for IL-18 can be used as an inhibitor of IL-18 induced inflammatory responses. Accordingly, an embodiment of the present invention includes the extracellular portion Preferred DNA and amino acid embodiments of the present invention include the coding region of SEQ ID NO: 1 and SEQ ID NO:6 and the amino acids encoded by SEQ ID NO:1 and SEQ ID NO:6, shown in SEQ ID NO:2 and SEQ ID NO:7, respectively. Additional preferred embodiments are domains of the ACPL amino acid sequences and the nucleotide sequences that encode the domains. For SEQ ID NO:7: the domains include: an extracellular domain of 356 amino acids (residues 1-356 from N- to C-terminus of SEQ ID NO:7) that includes a signal peptide of 14 amino acids (residues 1-14 of SEQ ID NO:7); a transmembrane region of 25 amino acids (residues 357-381 of SEQ ID NO:7) and a cytoplasmic domain of amino acids (residues 382-599 of SEQ ID NO:7). For SEQ ID NO:2, the ACPL amino acid sequence domains of the present invention include: an extracellular domain of 356 amino acids (residues 1-356 from N- to C-terminus of SEQ ID NO:2) that includes a signal peptide of 14 amino acids (residues 1-14 of SEQ ID NO:2); a transmembrane region of 24 amino acids (residues 357-380 of SEQ ID NO:2) and a cytoplasmic domain of amino acids (residues 381-614 of SEQ ID NO:2).

The discovery of the nucleic acids of the invention enables the construction of expression vectors comprising nucleic acid sequences encoding polypeptides; host cells transfected or transformed with the expression vectors; and isolated and purified biologically active polypeptides and fragments thereof. Further, the discovery of the disclosed nucleic acids, and fragments or oligonucleotides thereof, allows their use as probes to identify nucleic acids encoding proteins having homology with IL-1 and to identify nucleic acids encoding proteins having a role in IL-18 mediated responses. Moreover, nucleic acids and oligonucleotides of the present invention find use in mapping DNA on human chromosome 2q and to identify genes associated with certain diseases, syndromes or other human conditions associated with human chromosome number 2q. The table below identifies a number of such diseases, syndromes, or conditions.

| Location | Gene Name | Disease Name |
| --- | --- | --- |
| 2q11 | Cyclic nucleotide-gated channel, alpha-3 | Achromatopsia-2 |
| 2q11 | Dual-specificity phosphatase 2 | |
| 2q11 | Tibial muscular dystrophy | Tibial muscular dystrophy |
| 2q11–q12 | RAN-binding protein 2-like 1 | |
| 2q11–q13 | Ectodermal dysplasia-3, anhidrotic | Ectodermal dysplasia-3, anhidrotic |
| 2q11–q14 | Solute carrier family 20, phosphate transporter, member 1 (Gibbon ape leukemia virus receptor-1) | |
| 2q11–q11.2 | Sulfotransferase 1C1 | |
| 2q11.2 | Barren, Drosophila, homolog of, 1 | |
| 2q11.2 | Solute carrier family 9 (sodium/hydrogen exchanger, isoform 2) | |
| 2q11.2–q12 | Lymphoid nuclear protein related to AF4 | |
| 2q12 | Interleukin-1 receptor, type I | |
| 2q12 | zeta-chain associated protein kinase, 70 kD (syk-related tyrosine kinase) | Selective T cell defect |
| 2q12–q14 | Four and a half LIM domains-2 (down-regulated in rhabdomyosarcoma LIM protein) | |
| 2q12–q14 | Immunoglobulin orphon (transposed element) 1 | |
| 2q12–q14 | Paired box homeotic gene-8 congenital, | hypothyroid, due to thyroid dysgenesis orhypoplasia |
| 2q12–q21 | Diazepam-binding inhibitor | |
| 2q12–q22 | Interleukin-1 receptor, type II | |
| 2q12–qter | Nucleolin | |
| 2q13 | BENE protein | |
| 2q13 | mal, T cell differentiation protein - like | |
| 2q13 | Nephronophthisis-1 (juvenile) | Nephronophthisis-1 (juvenile) |
| 2q13–q14 pro | Protein C (inactivator of coagulation factors Va and VIIIa) | Thrombophilia due to protein C deficiency Purpura fulminans,neonatal |
| 2q13–q21 | Engrailed-1 | |
| 2q14 | Amphiphysin-like (box-dependent MYC-interacting protein-1) | |
| 2q14 | GLI-Kruppel family member GLI2 (oncogene GLI2) | |
| 2q14 | Interleukin-1 alpha | |

The nucleic acids of the present invention enable the use of single-stranded sense or antisense oligonucleotides from the nucleic acids to inhibit expression of polynucleotide encoded by the ACPL gene. The polypeptides and soluble fragments of the present invention (e.g. extracellular domains of SEQ ID NO:2 and SEQ ID NO:7 and active fragments thereof) can be used to inhibit IL-18 mediated responses and to study processes associated with inducible protein expression systems that are based upon ACPL-dependent induction. Such systems can include, but are not limited to, ACPL-dependent induction of NFkB-mediated signaling in response to IL-18 stimulation and Ap-1-mediated signaling in response to IL-18 stimulation. Similarly, such processes include those that are associated with responses to the IL-18 induction of the MAP kinase family kinases JNK and p38.

Polypeptides and their fragmented peptides of the present invention find further use as molecular weight markers, as control reagents for peptide fragmentation, and as components of kits comprising these reagents. Additionally, the polypeptides and polypeptide fragments of the present invention are useful in the generation of antibodies. Antibodies so generated are encompassed by the present invention and are useful as therapeutics and in processes for purifying polypeptides and polypeptide fragments of the present invention.

Nucleic Acids

In one embodiment, the present invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd sed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1, SEQ ID NO:3, SEQ ID NO:6, or a suitable fragment thereof, as a probe.

The DNA molecules of the invention include full length genes as well as polynucleotides and fragments thereof. The full length gene may include the N-terminal signal peptide.

Other embodiments include DNA encoding a soluble form, e.g., encoding the extracellular domain of the protein, either with or without the signal peptide.

The nucleic acids of the invention are preferentially derived from human sources, but the invention includes those derived from non-human species, as well.

Due to the known degeneracy of the genetic code, wherein more than one codon can encode the same amino acid, a DNA sequence can vary from that shown in SEQ ID NO:1, SEQ ID NO:3 and SEQ ID NO:6 and still encode a polypeptide having the amino acid sequence of SEQ ID NO:2 and SEQ ID NO:7. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO: 1, SEQ ID NO:3 and SEQ ID NO:6; (b) DNA encoding the polypeptides of SEQ ID NO:2 and SEQ ID NO:7; (c) DNA capable of hybridization to a DNA of (a) or (b) under conditions of moderate stringency and which encode polypeptides having ACPL activity; (d) DNA capable of hybridization to a DNA of (a) or (b) under conditions of high stringency and which encode polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al. *Molecular Cloning: A Laboratory Manual*, 2 ed. Vol. 1, pp. 1.101-1.104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution(s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp 353-358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding an ACPL polypeptide, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

The skilled artisan will recognize that the above-described boundaries of ACPL polypeptide domains (e.g. the extracellular domain, signal peptide, transmembrane region, and cytoplastmic domain) are approximate and that the boundaries of the transmembrane region and the signal peptide (which may be predicted by using computer programs available for that purpose) may differ from those described above.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may include the cytoplasmic domain, or a portion thereof, as long as the polypeptide is secreted from the cell in which it is produced. Additional examples of soluble polypeptides are those lacking not only the cytoplasmic domain and transmembrane region, but also all or part of the above-described spacer region.

In general, the use of soluble forms is advantageous for certain applications. Purification of the polypeptides from recombinant host cells is facilitated, since the soluble polypeptides are secreted from the cells. Soluble polypeptides are generally more suitable for intravenous administration. Further, soluble polypeptides can be useful for inhibiting activity associated with ACPL binding proteins.

The invention also provides ACPL polypeptides and fragments, thereof that retain a desired biological activity (e.g. the extracellular domain). Particular embodiments are directed to polypeptide fragments that retain the ability to bind an ACPL binding protein or binding partner. Such a fragment may be a soluble polypeptide, as described above. In another embodiment, the polypeptides and fragments advantageously include regions that are conserved in the IL-1 receptor family as described above.

Also provided herein are polypeptide fragments comprising at least 20, or at least 30, contiguous amino acids of the sequence of SEQ ID NO:2 or SEQ ID NO:7. Fragments derived from the cytoplasmic domain find use in studies of signal transduction, and in regulating cellular processes associated with transduction of biological signals. Polypeptide fragments also may be employed as immunogens, in generating antibodies.

Variants

Naturally occurring variants as well as derived variants of the polypeptides and fragments are provided herein.

Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (SEQ ID NO:8), which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds to its binding protein or binding partner with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as E. coli, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain ACPL polypeptides. Such oligomers may be in the form of covalently-linked or non-covalently-linked multimers, including dimers, trimers, or higher oligomers. As noted above, preferred polypeptides are soluble and thus these oligomers may comprise soluble polypeptides. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four ACPL extracellular regions. Alternatively, fusion proteins can be prepared in which ACPL or a soluble fragment of ACPL, e.g. the extracellular region, and IL-1Rrp1 or a soluble fragment of IL-1Rrp1, e.g. the extracellular region, are substituted for the variable portion of an antibody heavy or light chain.

Peptide-linker Based Oligomers

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble ACPL polypeptides, separated by peptide linkers. Similarly, as described above, the fusion protein can include two ACPL polypeptides or fragments and two IL-1Rrp1 polypeptides or fragments.

Leucine-Zippers

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240: 1759, 1988). The products of the nuclear oncogenes fos and jun comprise zipper domains that preferentially form heterodimer (O'Shea et al., *Science* 245:646, 1989, Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547,1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci U.S.A.* 88:3523, 1991). Zipper domains have also been recently reported to play a role in oligomerization of heat-shock transcription factors (Rabindran et al., *Science* 259:230, 1993).

Zipper domains fold as short, parallel coiled coils (O'Shea et al., *Science* 254:539; 1991). The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated (abcdefg)$_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek: et al., *Int. J. Peptide Res.* 38:229, 1991). Lovejoy et al. (*Science* 259:1288, 1993) recently reported the synthesis of a triple-stranded a-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al (*Science* 262:1401, 26 Nov. 1993).

Examples of leucine zipper domains suitable for producing soluble oligomeric proteins are described in PCT application WO 94/10308, as well as the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267-278, 1994). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD) noted above, as described in Hoppe et al. (*FEBS Letters* 344:191, 1994) and in U.S. Pat. No. 5,716,805, hereby incorporated by reference in their entirety. This lung SPD-derived leucine zipper peptide comprises the amino acid sequence Pro Asp Val Ala Ser Leu Arg Gln Gln Val Glu Ala Leu Gln Gly Gln Val Gln His Leu Gln Ala Ala Phe Ser Gln Tyr.

Another example of a leucine zipper that promotes trimerization is a peptide comprising the amino acid sequence Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg, as described in U.S. Pat. No. 5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing oligomeric ACPL, including trimeric ACPL. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Production of Polypeptides and Fragments Thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid; an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant ACPL polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15-69). Additional protocols using commercially available reagents, such as Lipofectamine lipid reagent (Gibco/BRL) or Lipofectamine-Plus lipid reagent, can be used to transfect cells (Feigner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534 and PCT Application WO 97/25420) and the tripartite leader (TPL) and VA gene RNAs from Adenovirus 2 (Glngeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by PFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460, 846.

Isolation and Purification

The invention also includes methods of isolating and purifying ACPL polypeptides and fragments thereof.

The "isolated" polypeptides or fragments thereof encompassed by this invention are ACPL polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, recombinant ACPL polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising an ACPL polypeptide-binding protein, such as a monoclonal antibody generated against an ACPL polypeptide or fragment thereof, to affinity-purify expressed polypeptides. These, purified ACPL polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, an ACPL polypeptide-binding proteins, such as the anti-polypeptide antibodies of the invention or other proteins that may interact with ACPL polypeptide, can be bound to a solid phase support such as a column chromatography matrix or a similar substrate suitable for identifying, separating, or purifying cells that express polypeptides of the invention on their surface. Adherence of ACPL polypeptide-binding proteins to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having ACPL polypeptides on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing ACPL polypeptide-expressing cells first can be incubated with a biotinylated ACPL polypeptide-binding protein. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (including proteins, polypeptides, fragments, variants, oligomers, and other forms) may be tested for the ability to bind in any suitable assay, such as a conventional binding assay. To illustrate, the polypeptide may be labeled with a detectable reagent (e.g., a radionuclide, chromophore, enzyme that catalyzes a colorimetric or fluorometric reaction, and the like). The labeled polypeptide is contacted with cells expressing a suitable ACPL binding protein, e.g. an anti-ACPL antibody. The cells then are washed to remove unbound labeled polypeptide, and the presence of cell-bound label is determined by a suitable technique, chosen according to the nature of the label.

One example of a binding assay procedure is as follows. A recombinant expression vector containing an ACPL binding protein cDNA is constructed. CV1-EBNA-1 cells in 10 cm² dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, the transfected cells (about 4×10⁴ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion protein made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein/Fc, as well as in the presence of the Fc fusion protein and a 200-fold molar excess of unlabeled mouse anti-human IgG antibody.

Cell-bound $^{125}$I-antibody is quantified on a Packard Auto-gamma counter. Affinity calculations (Scatchard, *Ann. N.Y. Acad. Sci.* 51:660, 1949) are generated on RS/1 (BBN Software, Boston, Mass.) run on a Microvax computer.

Another type of suitable binding assay is a competitive binding assay. To illustrate, biological activity of an ACPL variant may be determined by assaying for the variant's ability to compete with the native protein for binding to an ACPL binding protein.

Competitive binding assays can be performed by conventional methodology. Reagents that may be employed in competitive binding assays include radiolabeled ACPL and intact cells expressing an ACPL binding protein (endogenous or recombinant) on the cell surface. For example, a radiolabeled soluble ACPL fragment can be used to compete with a soluble ACPL variant for binding to cell surface ACPL binding protein. Instead of intact cells, one could substitute a soluble ACPL binding protein/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radio-labeled soluble ACPL binding protein, such as a ACPL binding protein/Fc fusion protein, and intact cells expressing ACPL. Qualitative results can be obtained by competitive autoradiographic plate binding assays, while Scatchard plots (Scatchard, *Ann. N.Y. Acad. Sci.* 51:660, 1949) may be utilized to generate quantitative results.

Use of ACPL Nucleic Acid or Oligonucleotides

In addition to being used to express polypeptides as described above, the nucleic acids of the invention, including DNA, and oligonucleotides thereof can be used:

to identify human chromosome number 2q to map genes on human chromosome number 2q to identify genes associated with certain diseases, syndromes, or other conditions associated with human chromosome number 2q;

as single-stranded sense or antisense oligonucleotides, to inhibit expression of polypeptide encoded by the ACPL gene;

to help detect defective genes in an individual; and for gene therapy.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO: 1, SEQ ID NO:3 and SEQ ID NO:4 and SEQ ID NO:6 from other mammalian species are contemplated herein, probes based on the DNA sequence of SEQ ID NO: 1, SEQ ID NO:3, SEQ ID NO:4 and SEQ ID NO:6 may be used to screen cDNA libraries derived from other mammalian species using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Chromosome Mapping

All or a portion of the nucleic acids of SEQ ID NO: 1, SEQ ID NO:3, and SEQ ID NO:6, including oligonucleotides, can be used by those skilled in the art using well-known techniques to identify the human 2q, and the specific locus thereof, that contains the DNA of IL-1R family members, including IL-1 receptors I and II, ST2 and IL-1Rrp1. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization. First, PCR is performed using the Whitehead Institute/MIT Center for Genome Research Genebridge4 panel of 93 radiation hybrids. Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet. The data is scored and the chromosomal assignment and placement relative to known Sequence Tag Site (STS) markers on the radiation hybrid map is provided.

Identifying Associated Diseases

As set forth below, the DNA of SEQ ID NO:6 has been mapped to the chromosome 2q. That region is associated with specific diseases which include but are not limited to those identified in Table I, above. Thus, the nucleic acid of SEQ ID NO:6 or a fragment thereof can be used by one skilled in the art using well-known techniques to analyze abnormalities associated with gene mapping to chromosome 2q. This enables one to distinguish conditions in which this marker is rearranged or deleted. In addition, nucleotides of SEQ ID NO:6 or a fragment thereof can be used as a positional marker to map other genes of unknown location.

The DNA may be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Sense-Anti sense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of the DNA of SEQ ID NO: 1, SEQ ID NO:3, or SEQ ID NO:6. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced info a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Use of ACPL Polypeptides and Fragmented Polypeptides
  Uses include, but are not limited to, the following:
  Purifying proteins and measuring activity thereof
  Delivery Agents
  Therapeutic and Research Reagents
  Molecular weight and Isoelectric focusing markers
  Controls for peptide fragmentation
  Identification of unknown proteins
  Preparation of Antibodies
  Purification Reagents The polypeptides of the invention find use as a protein purification reagent. For example, ACPL polypeptides may be attached to a solid support material and used to purify ACPL binding proteins by affinity chromatography. In particular embodiments, a polypeptide (in any form described herein that is capable of binding to an ACPL binding protein) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express an ACPL binding protein on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing ACPL binding protein expressing cells are contacted with the solid phase having the polypeptides thereon. Cells expressing ACPL binding protein on the cell surface bind to the fixed polypeptides, and unbound cells then are washed away.

Alternatively, the polypeptides can be conjugated to a detectable moiety, then incubated with cells to be tested for binding protein expression. After incubation, unbound labeled matter is removed and the presence or absence of the detectable moiety on the cells is determined.

In a further alternative, mixtures of cells suspected of containing ACPL binding protein cells are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.,* 10D:239, 1986). Washing to remove unbound material, and the release of the bound cells, are performed using conventional methods.

Measuring Activity

Polypeptides also find use in measuring the biological activity of ACPL binding protein in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of an ACPL binding protein that has been stored at different temperatures, or produced in different cell types. The proteins also may be used to determine whether biological activity is retained after modification of an ACPL binding protein (e.g., chemical modification, truncation, mutation, etc.). The binding affinity of the modified ACPL binding protein is compared to that of an unmodified ACPL binding protein to detect any adverse impact of the modifications on biological activity of ACPL binding protein. The biological activity of an ACPL binding protein thus can be ascertained before it is used in a research study, for example.

Delivery Agents

The polypeptides also find use as carriers for delivering agents attached thereto to cells bearing an ACPL binding protein. The polypeptides thus can be used to deliver diagnostic or therapeutic agents to such cells (or to other cell types found to express ACPL binding protein on the cell surface) in in vitro or in vivo procedures.

Detectable (diagnostic) and therapeutic agents that may be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the polypeptide by any suitable conventional procedure. The polypeptide comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Therapeutic Agents

Polypeptides of the invention may be used in developing treatments for any disorder mediated (directly or indirectly) by defective, excessive or insufficient amounts of ACPL or any binding partners, including IL polypeptides. Isolated and purified ACPL polypeptides or a fragment thereof can also be useful itself as a therapeutic agent in inhibiting IL-1 and TNF signaling. Such therapeutic uses of ACPL can involve their administration by the instruction of the ACPL polypeptide or fragment into the intracellular environment by well-known means. One such mean is by encasing the protein in liposomes or coupling it to a monoclonal antibody targeted to a specific cell type.

The polypeptides may also be employed in inhibiting a biological activity of an ACPL binding protein, in in vitro or in vivo procedures. For example, an ACPL purified polypeptide or soluble fragment thereof may be used to inhibit binding of an ACPL binding protein to endogenous cell surface ACPL binding partner. Biological effects that result from the binding of binding partner to endogenous receptors thus are inhibited.

In addition, ACPL polypeptides may be administered to a mammal to treat a disorder mediated by an ACPL binding partner. Such binding partner-mediated disorders include conditions caused (directly or indirectly) or exacerbated by the binding partner.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble ACPL polypeptides, e.g. the extracellular domain of ACPL or biologically active fragments thereof that bind to the binding partner.

Compositions comprising an effective amount of an ACPL polypeptide or fragment thereof of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, intracellularly or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising nucleic acids in physiologically acceptable formulations are also contemplated. DNA may be formulated for injection, for example.

Research Agents

Another use of the polypeptide of the present invention is as a research tool for studying the biological effects that result from inhibiting ACPL binding partner/ACPL interactions on different cell types. Polypeptides also may be employed in in vitro assays for detecting ACPL binding partner or ACPL or the interactions thereof.

ACPL polypeptides, and antibodies against ACPL polypeptides can be used as reagents in a variety of research protocols. A sample of such research protocols are given in Sambrook et al. *Molecular Cloning: A Laboratory Manual*, 2 ed. Vol. 1-3, Cold Spring Harbor Laboratory Press, (1989). For example, these reagents can serve as markers for cell specific or tissue specific expression of RNA or proteins. Similarly, these reagents can be used to investigate constituitive and transient expression of ACPL RNA or polypeptides. ACPL DNA can be used to determine the chromosomal location of ACPL DNA and to map genes in relation to this chromosomal location. ACPL DNA can also be used to examine genetic heterogeneity and heredity through the use of techniques such as genetic fingerprinting, as well as to identify risks associated with genetic disorders. ACPL DNA can be further used to identify additional genes related to ACPL DNA and to establish evolutionary trees based on the comparison of sequences. ACPL DNA and polypeptides can be used to select for those genes or proteins that are homologous to ACPL DNA or polypeptides, through positive screening procedures such as Southern blotting and immunoblotting and through negative screening procedures such as subtraction.

ACPL polypeptides can also be used as a reagent to identify (a) any protein that ACPL polypeptide regulates, and (b) other proteins with which it might interact. ACPL polypeptides could be used by coupling recombinant protein to an affinity matrix, or by using them as a bait in the 2-hybrid system. ACPL polypeptides and fragments thereof can be used as reagents in the study of signaling pathways used by receptors of the IL-1R family and to block signaling by IL-18 and possibly other ligands of the IL-1 family.

Another embodiment of the invention relates to uses of ACPL to study cell signal transduction. ACPL polypeptides play a role in immune responses which includes cellular signal transduction. As such, alterations in the expression and/or activation of ACPL can have profound effects on a plethora of cellular processes. Expression of cloned ACPL, functionally inactive mutants of ACPL can be used to identify the role a particular protein plays in mediating specific signaling events.

Cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed functionally active versions of ACPL can be used in assays such as the yeast 2-hybrid assay to identify what substrate(s) were recognized and activated by ACPL binding partners. As such, these novel ACPL can be used as reagents to identify novel molecules involved in signal transduction pathways.

Furthermore, ACPL polypeptides and fragments thereof can be used as reagents in the study of the IL-18 signaling pathway as a reagent to block IL-18 signaling: The discovery that ACPL polypeptide plays a role in NFkB signaling allows the use of ACPL polypeptides in studies of NFkB signaling, particularly with regard to the induction of NFkB signaling by IL-18. The discovery of ACPL polypeptide and its role in NFkB signaling further allows its use as a reagent in research protocols to elucidate the role of IL-1Rrp1 and IL-18 in cell signaling.

IL-18 induces many additional signaling responses. Among such signaling responses is the induction of the MAP kinase family kinases JNK and p38. Thus, ACPL polypeptides and fragments thereof can be used as reagents in the study IL-18 induced signaling responses of the MAP kinase family kinases JNK and p38.

The discovery that ACPL polypeptide stimulates production of a specific protein in response to IL-18 allows the generation of inducible protein expression systems. In one embodiment, the gene encoding the protein of interest can be placed within a vector containing three NFkB sites mediating expression of the protein. The skilled artisan recognizes that many different vectors can be used to achieve expression linked to NFkB expression, depending upon the cell type desired for expression. As an example, $10^7$ S49.1 cells can be transfected by electroporation in 0.7 ml with 40 µg of a NFkB-linked expression vector and 20 µg of expression vectors encoding murine ACPL polypeptide and murine IL-1R-Rp1 at 960 µF and 320V. Cells can be incubated for 2 days and can then be stimulated with 40 ng/ml murine IL-18 (PeproTech). The addition of IL-18 can induce expression of the NFkB-linked gene 300-fold. It is understood that many different approaches can be used to acheive induction of protein expression using ACPL polypeptide and IL-18 stimulation, and that this embodiment in no way limits the scope of the invention.

Due to the regulated production of the NFkB-linked protein, the level of this protein within the cells can be modulated according to stimulation with IL-18. The use of a marker gene, such as luciferase, allows the elucidation of inhibitors and regulators of IL-18 stimulated NFkB signaling. Additionally, control of the level and timing of protein expression enables one skilled in the art to examine both the temporal and cumulative effects of the protein of interest. Antibodies against ACPL polypeptides can further be used to inhibit IL-18 stimulated NFkB signaling in these experiments, allowing a more detailed analysis of the steps involved in NFkB signaling.

The purified ACPL polypeptides according to the invention will facilitate the discovery of inhibitors of ACPL polypeptides. The use of a purified ACPL polypeptide in the screening of potential inhibitors thereof is important and can eliminate or reduce the possibility of interfering reactions with contaminants.

In addition, ACPL polypeptides can be used for structure-based design of ACPL polypeptide-inhibitors. Such structure-based design is also known as "rational drug design." The ACPL polypeptides can be three-dimensionally analyzed by, for example, X-ray crystallography, nuclear magnetic resonance or homology modeling, all of which are well-known methods. The use of ACPL polypeptide structural information in molecular modeling software systems to assist in inhibitor design and inhibitor-ACPL polypeptide interaction is also encompassed by the invention. Such computer-assisted modeling and drug design can utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of ACPL polypeptides for likely binding sites of substrates, synthesizing a new molecule that incorporates a predictive reactive site, and assaying the new molecule as described above.

Molecular Weight, Isoelectric Point Markers

The present invention further includes processes that utilize ACPL polypeptides as molecular weight markers to estimate the apparent molecular weight of a sample protein by gel electrophoresis. An isolated and purified mouse ACPL polypeptide molecular weight marker according to the invention has a molecular weight of approximately 70,048 Daltons in the absence of glycosylation. The ACPL polypeptide, together with a sample protein, can be resolved by denaturing polyacrylamide gel electrophoresis by conventional means (U. K. Laemmli, *Nature* 227:680-685, 1970) in two separate lanes of a gel containing sodium dodecyl sulfate and a concentration of acrylamide between 6-20%. Proteins on the gel can be visualized using a conventional staining procedure. The ACPL polypeptide molecular weight marker can be used as a molecular weight marker in the estimation of the apparent molecular weight of the sample protein. The unique amino acid sequence of mouse ACPL (SEQ ID NO:2) specifies a molecular weight of approximately 70,048 Daltons. Therefore, the ACPL polypeptide molecular weight marker serves particularly well as a molecular weight marker for the estimation of the apparent molecular weight of sample proteins that have apparent molecular weights close to 70,048 Daltons. The use of this polypeptide molecular weight marker allows an increased accuracy in the determination of apparent molecular weight of proteins that have apparent molecular weights close to 70,048 Daltons. Similarly, human ACPL polypeptide (SEQ ID NO:7) can be used as a molecular weight marker for the estimation of the apparent molecular weight of sample proteins. It is understood of course that many different techniques can be used for the determination of the molecular weight of a sample protein using ACPL polypeptides and that this embodiment in no way limits the scope of the invention.

Another preferred embodiment of the invention is the use of ACPL fragmented peptide molecular weight markers, generated by chemical fragmentation of ACPL polypeptide, as molecular weight markers to estimate the apparent molecular weight of a sample protein by gel electrophoresis. Isolated and purified ACPL polypeptide can be treated with cyanogen bromide under conventional conditions that result in fragmentation of the ACPL polypeptide molecular weight marker by specific hydrolysis on the carboxyl side of the methionine residues within the ACPL polypeptide (E. Gross, *Methods in Enz.* 11:238-255, 1967). Due to the unique amino acid sequence of the ACPL polypeptide, the fragmentation of ACPL polypeptide molecular weight markers with cyanogen bromide generates a unique set of ACPL fragmented peptide molecular weight markers. For instance, human and mouse ACPL polypeptides will each generate a unique set of ACPL fragmented peptide molecular weight markers. The sizes of these molecular weight markers can be predicted using available computer programs. The distribution of methionine residues determines the number of amino acids in each peptide and the unique amino acid composition of each peptide determines its molecular weight.

The unique set of ACPL fragmented peptide molecular weight markers generated by treatment of mouse ACPL polypeptide with cyanogen bromide comprises 10 fragmented peptides of at least 10 amino acids in size. The peptide encoded by amino acids 2-87 of SEQ ID NO:2 has a molecular weight of approximately 9,724 Daltons. The peptide encoded by amino acids 88-105 of SEQ ID NO:2 has a molecular weight of approximately 2,020 Daltons. The peptide encoded by amino acids 111-136 of SEQ ID NO:2 has a molecular weight of approximately 3,094 Daltons. The peptide encoded by amino acids 137-188 of SEQ ID NO:2 has a molecular weight of approximately 5,502 Daltons. The peptide encoded by amino acids 189-207 of SEQ ID NO:2 has a molecular weight of approximately 2,354 Daltons. The peptide encoded by amino acids 208-299 of SEQ ID NO:2 has a molecular weight of approximately 10,617 Daltons. The peptide encoded by amino acids 300-369 of SEQ ID NO:2 has a molecular weight of approximately 8,293 Daltons. The peptide encoded by amino acids 370-558 of SEQ ID NO:2 has a molecular weight of approximately 21,559 Daltons. The peptide encoded by amino acids 568-593 of SEQ ID NO:2 has a molecular weight of approximately 2,963 Daltons. The peptide encoded by amino acids 594-614 of SEQ ID NO:2 has a molecular weight of approximately 2,343 Daltons.

Therefore, cleavage of the mouse ACPL polypeptide by chemical treatment with cyanogen bromide generates a unique set of ACPL fragmented peptide molecular weight markers. The unique and known amino acid sequence of these ACPL fragmented peptides allows the determination of the molecular weight of these fragmented peptide molecular weight markers. In this particular case, ACPL fragmented peptide molecular weight markers have molecular weights of approximately 9,724; 2,020; 3,094; 5,502; 2,354; 10,617; 8,293; 21,559; 2,963; and 2,343 Daltons.

The ACPL fragmented peptide molecular weight markers, together with a sample protein, can be resolved by denaturing polyacrylamide gel electrophoresis by conventional means in two separate lanes of a gel containing sodium dodecyl sulfate and a concentration of acrylamide between 10-20%. Proteins on the gel can be visualized using a conventional staining procedure. The ACPL fragmented peptide molecular weight markers can be used as molecular weight markers in the estimation of the apparent molecular weight of the sample protein. The unique amino acid sequence of mouse ACPL specifies a molecular weight of approximately 9,724; 2,020; 3,094; 5,502; 2,354; 10,617; 8,293; 21,559; 2,963; and 2,343 Daltons for the ACPL fragmented peptide molecular weight markers. Therefore, the ACPL fragmented peptide molecular weight markers serve particularly well as molecular weight markers for the estimation of the apparent molecular weight of sample proteins that have apparent molecular weights close to 9,724; 2,020; 3,094; 5,502; 2,354; 10,617; 8,293; 21,559; 2,963; or 2,343 Daltons. Consequently, the use of these fragmented peptide molecular weight markers allows an increased accuracy in the determination of apparent molecular weight of proteins that have apparent molecular weights close to 9,724; 2,020; 3,094; 5,502; 2,354; 10,617; 8,293; 21,559; 2,963; or 2,343 Daltons. It is understood of course that the unique amino acid sequence of human ACPL polypeptide (SEQ ID NO: 13) can similarly be used to generate a unique set of human ACPL fragmented peptide molecular weight markers. The fragment sizes can readily be determined using available computer programs.

In a further embodiment, the sample protein and the ACPL polypeptide can be simultaneously, but separately, treated with cyanogen bromide under conventional conditions that result in fragmentation of the sample protein and the ACPL polypeptide by specific hydrolysis on the carboxyl side of the methionine residues within the sample protein and the ACPL polypeptide. As described above, the ACPL fragmented peptide molecular weight markers generated by cleavage of the ACPL polypeptide with cyanogen bromide have molecular weights of approximately 9,724; 2,020; 3,094; 5,502; 2,354; 10,617; 8,293; 21,559; 2,963; and 2,343 Daltons.

The fragmented peptides from both the ACPL polypeptide and the sample protein can be resolved by denaturing polyacrylamide gel electrophoresis by conventional means in two separate lanes of a gel containing sodium dodecyl sulfate and a concentration of acrylamide between 10-20%. Fragmented peptides on the gel can be visualized using a conventional staining procedure. The ACPL fragmented peptide molecular weight markers can be used as molecular weight markers in the estimation of the apparent molecular weight of the fragmented proteins derived from the sample protein. As discussed above, the ACPL fragmented peptide molecular weight markers serve particularly well as molecular weight markers for the estimation of the apparent molecular weight of fragmented peptides that have apparent molecular weights close to 9,724; 2,020; 3,094; 5,502; 2,354; 10,617; 8,293; 21,559; 2,963; or 2,343 Daltons. Consequently, the use of these ACPL fragmented peptide molecular weight markers allows an increased accuracy in the determination of apparent molecular weight of fragmented peptides that have apparent molecular weights close to 9,724; 2,020; 3,094; 5,502; 2,354; 10,617; 8,293; 21,559; 2,963; or 2,343 Daltons. The extent of fragmentation of the ACPL polypeptide is further used as a control to determine the conditions expected for complete fragmentation of the sample protein. It is understood of course that many chemicals could be used to fragment ACPL polypeptides and that this embodiment in no way limits the scope of the invention.

In another embodiment, unique sets of ACPL fragmented peptide molecular weight markers can be generated from ACPL polypeptide using enzymes that cleave the polypeptide at specific amino acid residues. Due to the unique nature of the amino acid sequence of the ACPL polypeptide, cleavage at different amino acid residues will result in the generation of different sets of fragmented peptide molecular weight markers.

An isolated and purified ACPL polypeptide can be treated with Achromobacter protease I under conventional conditions that result in fragmentation of the ACPL polypeptide by specific hydrolysis on the carboxyl side of the lysine residues within the ACPL polypeptide (T. Masaki et al., Biochim. Biophys. Acta 660:44-50, 1981; T. Masaki et al., Biochim. Biophys. Acta 660:51-55, 1981). Due to the unique amino acid sequence of the ACPL polypeptide, the fragmentation of ACPL polypeptide molecular weight markers with Achromobacter protease I generates a unique set of ACPL fragmented peptide molecular weight markers. The distribution of lysine residues determines the number of amino acids in each peptide and the unique amino acid composition of each peptide determines its molecular weight.

The unique set of ACPL fragmented peptide molecular weight markers generated by treatment of mouse ACPL polypeptide with Achromobacter protease I comprises 20 fragmented peptides of at least 10 amino acids in size. The generation of 20 fragmented peptides with this enzyme treatment of the ACPL polypeptide, as compared to the generation of 10 fragmented peptides with cyanogen bromide treatment of the ACPL polypeptide, clearly illustrate that the sizes of the fragmented peptide molecular weight markers will vary depending upon the fragmentation treatment utilized to fragment the ACPL polypeptide. Both the size and number of these fragments are dictated by the amino acid sequence of the ACPL polypeptide. Consequently, the number of fragmented peptides will also vary depending upon the fragmentation treatment utilized to fragment the ACPL polypeptide. In addition, fragmentation of human ACPL polypeptide (SEQ ID NO:7) will result in unique sets of fragmented peptides, dictated by the amino acid sequence of the ACPL polypeptide.

The peptide encoded by amino acids 1-16 of SEQ ID NO:2 has a molecular weight of approximately 1,897 Daltons. The peptide encoded by amino acids 17-28 of SEQ ID NO:2 has a molecular weight of approximately 1,236 Daltons. The peptide encoded by amino acids 30-55 of SEQ ID NO:2 has a molecular weight of approximately 3,100 Daltons. The peptide encoded by amino acids 56-71 of SEQ ID NO:2 has a molecular weight of approximately 1,721 Daltons. The peptide encoded by amino acids 79-141 of SEQ ID NO:2 has a molecular weight of approximately 7,285 Daltons. The peptide encoded by amino acids 148-192 of SEQ ID NO:2 has a molecular weight of approximately 4,893 Daltons. The peptide encoded by amino acids 203-238 of SEQ ID NO:2 has a molecular weight of approximately 4,123 Daltons. The peptide encoded by amino acids 250-266 of SEQ ID NO:2 has a molecular weight of approximately 1,866 Daltons. The peptide encoded by amino acids 267-283 of SEQ ID NO:2 has a molecular weight of approximately 1,989 Daltons. The peptide encoded by amino acids 292-305 of SEQ ID NO:2 has a molecular weight of approximately 1,757 Daltons. The peptide encoded by amino acids 313-333 of SEQ ID NO:2 has a molecular weight of approximately 2,601 Daltons. The peptide encoded by amino acids 334-353 of SEQ ID NO:2 has a molecular weight of approximately 2,324 Daltons. The peptide encoded by amino acids 355-395 of SEQ ID NO:2 has a molecular weight of approximately 4,765 Daltons. The peptide encoded by amino acids 406-471 of SEQ ID NO:2 has a molecular weight of approximately 7,339 Daltons. The peptide encoded by amino acids 473-507 of SEQ ID NO:2 has a molecular weight of approximately 3,885 Daltons. The peptide encoded by amino acids 513-527 of SEQ ID NO:2 has a molecular weight of approximately 1,785 Daltons. The peptide encoded by amino acids 529-539 of SEQ ID NO:2 has a molecular weight of approximately 1,282 Daltons. The peptide encoded by amino acids 543-561 of SEQ ID NO:2 has a molecular weight of approximately 2,329 Daltons. The peptide encoded by amino acids 562-576 of SEQ ID NO:2 has a molecular weight of approximately 1,855 Daltons. The peptide encoded by amino acids 596-612 of SEQ ID NO:2 has a molecular weight of approximately 1,858 Daltons.

Therefore, cleavage of the mouse ACPL polypeptide by enzymatic treatment with Achromobacter protease I generates a unique set of ACPL fragmented peptide molecular weight markers. The unique and known amino acid sequence of these fragmented peptides allows the determination of the molecular weight of these ACPL fragmented peptide molecular weight markers. In this particular case, these ACPL fragmented peptide molecular weight markers have molecular weights of approximately 1,897; 1,236; 3,100; 1,721; 7,285; 4,893; 4,123; 1,866; 1,989; 1,757; 2,601; 2,324; 4,765; 7,339; 3,885; 1,785; 1,282; 2,329; 1,855; and 1,858 Daltons.

Once again, the ACPL fragmented peptide molecular weight markers, together with a sample protein, can be resolved by denaturing polyacrylamide gel electrophoresis by conventional means in two separate lanes of a gel containing sodium dodecyl sulfate and a concentration of acrylamide between 10-20%. Proteins on the gel can be visualized using a conventional staining procedure. The ACPL fragmented peptide molecular weight markers can be used as molecular weight markers in the estimation of the apparent molecular weight of the sample protein. The ACPL fragmented peptide molecular weight markers serve particularly well as molecular weight markers for the estimation of the apparent molecular weight of proteins that have apparent molecular weights close to 1,897; 1,236; 3,100; 1,721; 7,285; 4,893; 4,123; 1,866; 1,989; 1,757; 2,601; 2,324; 4,765; 7,339; 3,885; 1,785; 1,282; 2,329; 1,855; or 1,858 Daltons. The use of these fragmented peptide molecular weight markers allows an increased accuracy in the determination of apparent molecular weight of proteins that have apparent molecular weights close to 1,897; 1,236; 3,100; 1,721; 7,285; 4,893; 4,123; 1,866; 1,989; 1,757; 2,601; 2,324; 4,765; 7,339; 3,885; 1,785; 1,282; 2,329; 1,855; or 1,858 Daltons. It is understood of course that the unique amino acid sequence of human ACPL polypeptide (SEQ ID NO: 13) can similarly be used to generate a unique set of fragmented peptide molecular weight markers. The fragment sizes can readily be determined using available computer programs.

In another embodiment, the sample protein and the ACPL polypeptide can be simultaneously, but separately, treated with Achromobacter protease I under conventional conditions that result in fragmentation of the sample protein and the ACPL polypeptide by specific hydrolysis on the carboxyl side of the lysine residues within the sample protein and the ACPL polypeptide. The ACPL fragmented peptide molecular weight markers and the fragmented peptides derived from the sample protein are resolved by denaturing polyacrylamide gel electrophoresis by conventional means in two separate lanes of a gel containing sodium dodecyl sulfate and a concentration of acrylamide between 10-20%. Fragmented peptides on the gel can be visualized using a conventional staining procedure. The ACPL fragmented peptide molecular weight markers can be used as molecular weight markers in the estimation of the apparent molecular weight of the sample protein. The ACPL fragmented peptide molecular weight markers serve particularly well as molecular weight markers for the estimation of the apparent molecular weight of fragmented peptides that have apparent molecular weights close to 1,897; 1,236; 3,100; 1,721; 7,285; 4,893; 4,123; 1,866; 1,989; 1,757; 2,601; 2,324; 4,765; 7,339; 3,885; 1,785; 1,282; 2,329; 1,855; or 1,858 Daltons. The use of these ACPL fragmented peptide molecular weight markers allows an increased accuracy in the determination of apparent molecular weight of fragmented peptides that have apparent molecular weights close to 1,897; 1,236; 3,100; 1,721; 7,285; 4,893; 4,123; 1,866; 1,989; 1,757; 2,601; 2,324; 4,765; 7,339; 3,885; 1,785; 1,282; 2,329; 1,855; or 1,858 Daltons. The extent of fragmentation of the ACPL polypeptide is further used as a control to determine the conditions expected for complete fragmentation of the sample protein. It is understood of course that many enzymes could be used to fragment ACPL polypeptides and that this embodiment in no way limits the scope of the invention.

In another embodiment, monoclonal and polyclonal antibodies against ACPL polypeptides can be generated. Balb/c mice can be injected intraperitoneally on two occasions at 3 week intervals with 10 μg of isolated and purified ACPL polypeptide or peptides based on the amino acid sequence of ACPL polypeptides in the presence of RIBI adjuvant (RIBI Corp., Hamilton, Mont.). Mouse sera are then assayed by conventional dot blot technique or antibody capture (ABC) to determine which animal is best to fuse. Three weeks later, mice are given an intravenous boost of 3 μg of the ACPL polypeptide or peptides, suspended in sterile PBS. Three days later, mice are sacrificed and spleen cells fused with Ag8.653 myeloma cells (ATCC) following established protocols. Briefly, Ag8.653 cells are washed several times in serum-free media and fused to mouse spleen cells at a ratio of three spleen cells to one myeloma cell. The fusing agent is 50% PEG: 10% DMSO (Sigma). Fusion is plated out into twenty 96-well flat bottom plates (Corning) containing HAT supplemented DMEM media and allowed to grow for eight days. Supernatants from resultant hybridomas are collected and added to a 96-well plate for 60 minutes that is first coated with goat anti-mouse Ig. Following washes, $^{125}$I-ACPL polypeptide or peptides are added to each well, incubated for 60 minutes at room temperature, and washed four times. Positive wells can be subsequently detected by autoradiography at −70 C using Kodak X-Omat S film. Positive clones can be grown in bulk culture and supernatants are subsequently purified over a Protein A column (Pharmacia). It is understood of course that many techniques could be used to generate antibodies against ACPL polypeptides and fragmented peptides thereof and that this embodiment in no way limits the scope of the invention.

In another embodiment, antibodies generated against ACPL polypeptides and fragmented peptides thereof can be used in combination with ACPL polypeptide or fragmented peptide molecular weight markers to enhance the accuracy in the use of these molecular weight markers to determine the apparent molecular weight and isoelectric point of a sample protein. ACPL polypeptide or fragmented peptide molecular weight markers can be mixed with a molar excess of a sample protein and the mixture can be resolved by two dimensional electrophoresis by conventional means. Polypeptides can be transferred to a suitable protein binding membrane, such as nitrocellulose, by conventional means.

Polypeptides on the membrane can be visualized using two different methods that allow a discrimination between the sample protein and the molecular weight markers. ACPL polypeptide or fragmented peptide molecular weight markers can be visualized using antibodies generated against these markers and conventional immunoblotting techniques. This detection is performed under conventional conditions that do not result in the detection of the sample protein. It is understood that it may not be possible to generate antibodies against all ACPL polypeptide fragments, since small peptides may not contain immunogenic epitopes. It is further understood that not all antibodies will work in this assay;

however, those antibodies which are able to bind ACPL polypeptides and fragments can be readily determined using conventional techniques.

The sample protein is visualized using a conventional staining procedure. The molar excess of sample protein to ACPL polypeptide or fragmented peptide molecular weight markers is such that the conventional staining procedure predominantly detects the sample protein. The level of ACPL polypeptide or fragmented peptide molecular weight markers is such as to allow little or no detection of these markers by the conventional staining method. The preferred molar excess of sample protein to ACPL polypeptide molecular weight markers is between 2 and 100,000 fold. More preferably, the preferred molar excess of sample protein to ACPL polypeptide molecular weight markers is between 10 and 10,000 fold and especially between 100 and 1,000 fold.

The ACPL polypeptide or fragmented peptide molecular weight markers can be used as molecular weight and isoelectric point markers in the estimation of the apparent molecular weight and isoelectric point of the sample protein. The ACPL polypeptide or fragmented peptide molecular weight markers serve particularly well as molecular weight and isoelectric point markers for the estimation of apparent molecular weights and isoelectric points of sample proteins that have apparent molecular weights and isoelectric points close to that of the ACPL polypeptide or fragmented peptide molecular weight markers. The ability to simultaneously resolve the ACPL polypeptide or fragmented peptide molecular weight markers and the sample protein under identical conditions allows for increased accuracy in the determination of the apparent molecular weight and isoelectric point of the sample protein. This is of particular interest in techniques, such as two dimensional electrophoresis, where the nature of the procedure dictates that any markers should be resolved simultaneously with the sample protein.

In another embodiment, ACPL polypeptide or fragmented peptide molecular weight markers can be used as molecular weight and isoelectric point markers in the estimation of the apparent molecular weight and isoelectric point of fragmented peptides derived by treatment of a sample protein with a cleavage agent. It is understood that many techniques can be used for the determination of molecular weight and isoelectric point of a sample protein and fragmented peptides thereof using ACPL polypeptide molecular weight markers and peptide fragments thereof and that this embodiment in no way limits the scope of the invention.

ACPL polypeptide molecular weight markers encompassed by invention can have variable molecular weights, depending upon the host cell in which they are expressed. Glycosylation of ACPL polypeptide molecular weight markers and peptide fragments thereof in various cell types can result in variations of the molecular weight of these markers, depending upon the extent of modification. The size of ACPL polypeptide molecular weight markers can be most heterogeneous with fragments of ACPL polypeptide derived from the extracellular portion of the polypeptide. Consistent molecular weight markers can be obtained by using polypeptides derived entirely from the transmembrane and cytoplasmic regions, pretreating with N-glycanase to remove glycosylation, or expressing the polypeptides in bacterial hosts.

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. The size of these pieces can be most heterogeneous with fragments of polypeptide derived from the extracellular portion of the polypeptide. Consistent polypeptides and peptide fragments can be obtained by using polypeptides derived entirely from the transmembrane and cytoplasmic regions, pretreating with N-glycanase to remove glycosylation, or expressing the polypeptides in bacterial hosts.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

The polypeptides and the resultant fragmented peptides can be analyzed by methods including sedimentation, electrophoresis, chromatography, and mass spectrometry to determine their molecular weights. Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, Nature 227:680-685, 1970). Conventionally, the method uses two separate lanes of a gel containing sodium dodecyl sulfate and a concentration of acrylamide between 6-20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, Biology of Microorganisms 76-77 (Prentice Hall, 6d ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., J. Biol. Chem. 252:1102-1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Henzel et al., Proc. Natl. Acad. Sci. USA 90:5011-5015, 1993; D. Fenyo et al., Electrophoresis 19:998-1005, 1998). A variety of computer software programs to facilitate these comparisons are accessible via the Internet, such as Protein Prospector, Multildent, PeptideSearch, and ProFound. These programs allow the user to specify the cleavage agent and the molecular weights of the fragmented peptides within a designated tolerance. The programs compare observed molecular weights to predicted peptide molecular weights derived from sequence databases to assist in determining the identity of the unknown protein.

In addition, a polypeptide or peptide digest can be sequenced using tandem mass spectrometry (MS/MS) and the resulting sequence searched against databases (J. K. Eng, et al., J. Am. Soc. Mass Spec. 5:976-989 (1994); M. Mann and M. Wilm, Anal. Chem. 66:4390-4399 (1994); J. A. Taylor and R. S. Johnson, Rapid Comm. Mass Spec. 11:1067-1075 (1997)). Searching programs that can be used in this process exist on the Internet, such as Lutefisk 97, and the Protein Prospector, Peptide Search and ProFound programs described above.

Therefore, adding the sequence of a gene and its predicted protein sequence and peptide fragments to a sequence database can aid in the identification of unknown proteins using mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and $F(ab')_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to its binding partner may be used to inhibit a biological activity that results from such binding. Such blocking antibodies may be identified using any suitable assay procedure, such as by testing antibodies for the ability to inhibit binding of ACPL to certain cells expressing the binding partner. Alternatively, blocking antibodies may be identified in assays for the ability to inhibit a biological effect that results from binding of an ACPL binding partner to target cells. Antibodies may be assayed for the ability to inhibit binding partner-mediated activity.

Such an antibody may be employed in an in vitro procedure, or administered in vivo to inhibit a biological activity mediated by the entity that generated the antibody. Disorders caused or exacerbated (directly or indirectly) by the interaction of an ACPL binding partner with cell surface binding partner receptor thus may be treated. A therapeutic method involves in vivo administration of a blocking antibody to a mammal in an amount effective in inhibiting a binding partner-mediated biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to cell surface binding partner, induce biological effects (e.g., transduction of biological signals) similar to the biological effects induced when an ACPL binding partner binds to cell surface ACPL. Agonistic antibodies may be used to induce IL-18 mediated activity.

Compositions comprising an antibody that is directed against ACPL, and a physiologically acceptable diluent, excipient, or carrier, are provided herein. Suitable components of such compositions are as described above for compositions containing ACPL proteins.

Also provided herein are conjugates comprising a detectable (e.g., diagnostic) or therapeutic agent, attached to the antibody. Examples of such agents are presented above. The conjugates find use in in vitro or in vivo procedures.

The following examples are provided to further illustrate particular embodiments of the invention, and are not to be construed as limiting the scope of the present invention. The specification is most thoroughly understood in light of the teachings of the references cited within the specification, which are hereby incorporated by reference. The embodiments within the specification and the following Examples provide an illustration of embodiments of the invention and should not be construed to limit the scope of the invention. The skilled artisan recognizes many other embodiments are encompassed by the claimed invention. In the following Examples, all methods described are conventional unless otherwise specified.

EXAMPLE 1

Isolation of the mouse Nucleic Acid

A mouse ACPL cDNA was isolated by searching the expressed sequence tag data base discovering the IMAGE clone 640615 (GenBank Accession number AA203097) has homology to IL-1RAcP. IMAGE clone 640615 was obtained, labeled with $^{32}$P by random priming and used to probe an EL46.1 (mouse thymocyte) cDNA library. The hybridization was carried out at 42° C. in hybridization solution containing 50% formamide. After the full-length open reading frame was defined by an EL46.1cDNA clone, it was verified by obtaining independent isolates from 7B9 (mouse T cell) and LDA11 (mouse bone marrow stromal) cDNA libraries using PCR amplification. Primers corresponded to nucleotides −15 to +13 and nucleotides 1892 to 1916 (relative to the initiating ATG being +1 to +3) of the mouse ACPL nucleotide sequence.

EXAMPLE 2

Isolation of Human ACPL Nucleic Acid Sequence

A human cDNA clone, termed QQ1352, obtained by random sequencing of an NK cell library, was found to have a high degree of homology to the murine ACPL isolated as described in Example 1. The clone was used as a probe to isolate human ACPL clones from peripheral blood lymphocyte, peripheral blood T cell, and NK cDNA libraries. The region of clone QQ1352 that was used as a probe was homologous to mouse ACPL nucleotides 1196-11753. A full-length c lone was not obtained from any of the libraries so vector-anchored PCR was carried out in each of the libraries to obtain the 5' end of the open reading frame (SEQ ID NO:6)

EXAMPLE 3

Determining Chromosome Map Position

The chromosome map position of human ACPL was determined by radiation hybrid mapping using the Stanford G3 Radiation Hybrid Panel (Research Genetics). The primers were selected for their homology to IL-1R. Amplification was carried out under standard PCR conditions for 40 cycles.

The results placed human ACPL on chromosome 2, most closely linked to AFM316tg5, with a logarithm of odds score of 12.72. This is the same region of chromosome 2 to which IL-1R type 1, II-1R type II, IL-1R-rp1, and T1/ST2 have been mapped.

EXAMPLE 4

Northern Blot Analysis

A human multiple tissue blot was purchased from CLONTECH laboratories, Inc. and contained 2 µg of mRNA from normal human spleen, thymus, prostate, testis, ovary, small intestine, colon, and peripheral blood leukocyte. This was hybridized overnight with a 32P-labeled antisense human ACPL riboprobe in hybridization buffer containing 50% formamide at 63° C. and then washed at 68° C. in 0.1×SSC/ 0.1% SDS. After exposure, the blot was rehybridized with a random-prime labeled probe against β-actin for standardization.

The results demonstrated that human ACPL is expressed strongly in peripheral blood leukocytes and spleen. To a less extent, human ACPL is expressed in colon. The results further demonstrated that human ACPL is weakly expressed in prostate and small intestine mRNA. The predominant mRNA product was approximately 3.8 kilobases, with minor bnds at approximately 2.6 and 8.0 kilobases. Expression was also detected in lung mRNA by Northern analysis.

EXAMPLE 5

Expressing ACPL polypeptide and ACPL:FC Fusions

To express mouse and human ACPL polypeptides, full-length mouse and human ACPL nucleotide sequences were generated by PCR and cloned into pDC304, a variant of pDC302. For expressing human ACPL:Fc fusion protein, the extracellular portion of the human ACPL expression vector (amino acids 1-356) was joined to the CH2 and CH3 domains of human IgG1 and was generated as described in Baum et al, *EMBO J.* 13:3992-4001 (1994).

EXAMPLE 6

Induction of NFkB through ACPL polypeptide in COS and S49 cells

In order to determine whether mouse ACPL polypeptide (SEQ ID NO:2) was a receptor involved in IL-18 signaling, ACPL polypeptide was overexpressed in COS cells and S49.1 cells, and the effect of IL-18 stimulation on NFkB activation was assessed. COS-7 cells were transfected by the DEAE/Dextran method in a 12-well format. Each well was transfected with a total of 200 ng of expression vectors encoding receptor(s) and 800 ng of a NFkB-Luc reporter plasmid, which contains 3 NFkB sites mediating luciferase expression. Approximately $10^7$ S49.1 cells were transfected by electroporation in 0.7 ml with 40 µg of the NFkB-Luc reporter plasmid, and a total of 20 μg of expression vectors encoding receptors. Electroporations were performed at 960 μF and 320V.

Cells were incubated for 2 days, and then stimulated with 40 ng/ml murine IL-18 (PeproTech) for 4 hours. Cells were washed, lysed, and assayed for luciferase activity using Luciferase Assay Reagents (Promega Corp.) according to the manufacturer's instructions.

Cells transfected with vector alone, expression vector encoding IL-Rrp1 alone, or expression vector encoding ACPL polypeptide alone were not responsive to IL-18 stimulation. Furthermore, no function of ACPL in IL-1 signaling was detected when the expression vector encoding the receptor was transfected alone, or in combination with an expression vector encoding IL-1R type 1 or IL-1RAcP. However, the addition of IL-18 to cells cotransfected with expression vectors encoding IL-1Rrp1 and ACPL polypeptide induced expression of the NFkB-linked gene 10-fold in COS cells and 300-fold in S49 cells. This dramatic stimulation of NFkB activity indicates that ACPL polypeptide is a component of the IL-18 receptor that cooperates synergistically with IL-1Rrp1 to induce NFkB signaling in response to IL-18 stimulation.

EXAMPLE 7

Activation of JNK Activity

The induction of JNK activity is a downstream signaling event in the IL-1 pathway. Similar to the induction of NFκB experiment above, it was examined whether ACPL alone or in combination with IL-1Rrp1 was capable of mediating the indcution of JNK activity by IL-18. Activation of JNK activity was assessed as described in Bird et al. *J. Biol. Chem.* 269:31836-31844, 1994. Two (2) days post-transfection, COS7 cells were simulated with IL-18 for 15 minutes, lysed, and immunoprecipitated with a combination of two anti-JNK antibodies (c-17 and FL, Santa Cruz Biotaechnology, Inc). This immunocomplex was assayed for activity by addition of glutathione S-transferase-c-Jun (Upstate Biotechnology, Inc.) and $[\gamma-^{32}]$ATP in kinase buffer. The reaction was allowed to proceed for 30 minutes at room temperature, after which Laemmli Loading buffer was added to stop the reaction, and products were electrophoresed on a 4-20% acrylamide getl, stained, dried, and analyzed on a PhosphorImager.

Similar to the results obtained regarding activation of NFκB, JNK activity was induced only by IL-18 in COS7 cells when IL-1R-Rp1 and ACPL were coexpressed.

What is claimed is:

1. A method for blocking IL-18-induced NF$_k$B activation in a mammal, the method comprising administering to a mammal an antibody that binds to a polypeptide consisting of amino acids 15-356 of SEQ ID NO:7, wherein the antibody blocks IL-18 stimulation of NF$_k$B signaling.

2. The method of claim 1, wherein the antibody is a monoclonal antibody.

3. The method of claim 2, wherein the monoclonal antibody is a humanized antibody.

4. The method of claim 3, wherein the mammal is a human.

5. A method for blocking IL-18-induced JNK activation in a mammal, the method comprising administering to a mammal an antibody that binds to a polypeptide consisting of amino acids 15-356 of SEQ ID NO:7, wherein the antibody blocks IL-18 induction of JNK signaling.

6. The method of claim 5, wherein the antibody is a monoclonal antibody.

7. The method of claim 6, wherein the monoclonal antibody is a humanized antibody.

8. The method of claim 7, wherein the mammal is a human.

* * * * *

```
                        SEQUENCE LISTING

<160> NUMBER OF SEQ ID NOS: 7

<210> SEQ ID NO 1
<211> LENGTH: 1845
<212> TYPE: DNA
<213> ORGANISM: Mus sp.
<220> FEATURE:
<221> NAME/KEY: CDS
<222> LOCATION: (1)..(1845)
<223> OTHER INFORMATION:

<400> SEQUENCE: 1 atg ctc tgt ttg ggc tgg gtg ttt ctt tgg ttt gtt gca gga gag aag        48
Met Leu Cys Leu Gly Trp Val Phe Leu Trp Phe Val Ala Gly Glu Lys
1               5                   10                  15 acc aca gga ttt aat cat tca gct tgt gcc acc aaa aaa ctt ctg tgg        96
Thr Thr Gly Phe Asn His Ser Ala Cys Ala Thr Lys Lys Leu Leu Trp
            20                  25                  30 aca tat tct gca agg ggt gca gag aat ttt gtc cta ttt tgt gac tta       144
Thr Tyr Ser Ala Arg Gly Ala Glu Asn Phe Val Leu Phe Cys Asp Leu
        35                  40                  45 caa gag ctt cag gag caa aaa ttc tcc cat gca agt caa ctg tca cca       192
Gln Glu Leu Gln Glu Gln Lys Phe Ser His Ala Ser Gln Leu Ser Pro
    50                  55                  60 aca caa agt cct gct cac aaa cct tgc agt ggc agt cag aag gac cta       240
Thr Gln Ser Pro Ala His Lys Pro Cys Ser Gly Ser Gln Lys Asp Leu
65                  70                  75                  80 tct gat gtc cag tgg tac atg caa cct cgg agt gga agt cca cta gag       288
Ser Asp Val Gln Trp Tyr Met Gln Pro Arg Ser Gly Ser Pro Leu Glu
                85                  90                  95 gag atc agt aga aac tct ccc cat atg cag agt gaa ggc atg ctg cat       336
Glu Ile Ser Arg Asn Ser Pro His Met Gln Ser Glu Gly Met Leu His
            100                 105                 110 ata ttg gcc cca cag acg aac agc att tgg tca tat att tgt aga ccc       384
Ile Leu Ala Pro Gln Thr Asn Ser Ile Trp Ser Tyr Ile Cys Arg Pro
        115                 120                 125
```

-continued

```
aga att agg agc ccc cag gat atg gcc tgt tgt atc aag aca gtc tta      432
Arg Ile Arg Ser Pro Gln Asp Met Ala Cys Cys Ile Lys Thr Val Leu
    130                 135                 140 gaa gtt aag cct cag aga aac gtg tcc tgt ggg aac aca gca caa gat      480
Glu Val Lys Pro Gln Arg Asn Val Ser Cys Gly Asn Thr Ala Gln Asp
145                 150                 155                 160 gaa caa gtc cta ctt ctt ggc agt act ggc tcc att cat tgt ccc agt      528
Glu Gln Val Leu Leu Leu Gly Ser Thr Gly Ser Ile His Cys Pro Ser
                165                 170                 175 ctc agc tgc caa agt gat gta cag agt cca gag atg acc tgg tac aag      576
Leu Ser Cys Gln Ser Asp Val Gln Ser Pro Glu Met Thr Trp Tyr Lys
            180                 185                 190 gat gga aga cta ctt cct gag cac aag aaa aat cca att gag atg gca      624
Asp Gly Arg Leu Leu Pro Glu His Lys Lys Asn Pro Ile Glu Met Ala
        195                 200                 205 gat att tat gtt ttt aat caa ggc ttg tat gta tgt gat tac aca cag      672
Asp Ile Tyr Val Phe Asn Gln Gly Leu Tyr Val Cys Asp Tyr Thr Gln
    210                 215                 220 tca gat aat gtg agt tcc tgg aca gtc cga gct gtg gtt aaa gtg aga      720
Ser Asp Asn Val Ser Ser Trp Thr Val Arg Ala Val Val Lys Val Arg
225                 230                 235                 240 acc att ggt aag gac atc aat gtg aag ccg gaa att ctg gat ccc att      768
Thr Ile Gly Lys Asp Ile Asn Val Lys Pro Glu Ile Leu Asp Pro Ile
                245                 250                 255 aca gat aca ctg gac gta gag ctt gga aag cct tta act ctc ccc tgc      816
Thr Asp Thr Leu Asp Val Glu Leu Gly Lys Pro Leu Thr Leu Pro Cys
            260                 265                 270 aga gta cag ttt ggc ttc caa aga ctt tca aag cct gtg ata aag tgg      864
Arg Val Gln Phe Gly Phe Gln Arg Leu Ser Lys Pro Val Ile Lys Trp
        275                 280                 285 tat gtc aaa gaa tct aca cag gag tgg gaa atg tca gta ttt gag gag      912
Tyr Val Lys Glu Ser Thr Gln Glu Trp Glu Met Ser Val Phe Glu Glu
    290                 295                 300 aaa aga att caa tcc act ttc aag aat gaa gtc att gaa cgt acc atc      960
Lys Arg Ile Gln Ser Thr Phe Lys Asn Glu Val Ile Glu Arg Thr Ile
305                 310                 315                 320 ttc ttg aga gaa gtt acc cag aga gat ctc agc aga aag ttt gtt tgc     1008
Phe Leu Arg Glu Val Thr Gln Arg Asp Leu Ser Arg Lys Phe Val Cys
                325                 330                 335 ttt gcc cag aac tcc att ggg aac aca aca cgg acc ata cgg ctg agg     1056
Phe Ala Gln Asn Ser Ile Gly Asn Thr Thr Arg Thr Ile Arg Leu Arg
            340                 345                 350 aag aag gaa gag gtg gtg ttt gta tac atc ctt ctc ggc acg gcc ttg     1104
Lys Lys Glu Glu Val Val Phe Val Tyr Ile Leu Leu Gly Thr Ala Leu
        355                 360                 365 atg ctg gtg ggc gtt ctg gtg gca gct gct ttc ctc tac tgg tac tgg     1152
Met Leu Val Gly Val Leu Val Ala Ala Ala Phe Leu Tyr Trp Tyr Trp
    370                 375                 380 att gaa gtt gtc ctg ctc tgt cga acc tac aag aac aaa gat gag act     1200
Ile Glu Val Val Leu Leu Cys Arg Thr Tyr Lys Asn Lys Asp Glu Thr
385                 390                 395                 400 ctg ggg gat aag aag gaa ttc gat gca ttt gta tcc tac tcg aat tgg     1248
Leu Gly Asp Lys Lys Glu Phe Asp Ala Phe Val Ser Tyr Ser Asn Trp
                405                 410                 415 agc tct cct gag act gac gcc gtg gga tct ctg agt gag gaa cac ctg     1296
Ser Ser Pro Glu Thr Asp Ala Val Gly Ser Leu Ser Glu Glu His Leu
            420                 425                 430 gct ctg aat ctt ttc ccg gaa gtg cta gaa gac acc tat ggg tac aga     1344
Ala Leu Asn Leu Phe Pro Glu Val Leu Glu Asp Thr Tyr Gly Tyr Arg
```

```
                435                 440                 445
ttg tgt ttg ctt gac cga gat gtg acc cca gga gga gtg tat gca gat    1392
Leu Cys Leu Leu Asp Arg Asp Val Thr Pro Gly Gly Val Tyr Ala Asp
    450                 455                 460 gac att gtg agc atc att aag aaa agc cga aga gga ata ttt atc ctg    1440
Asp Ile Val Ser Ile Ile Lys Lys Ser Arg Arg Gly Ile Phe Ile Leu
465                 470                 475                 480 agt ccc agc tac ctc aat gga ccc cgt gtc ttt gag cta caa gca gca    1488
Ser Pro Ser Tyr Leu Asn Gly Pro Arg Val Phe Glu Leu Gln Ala Ala
                485                 490                 495 gtg aat ctt gcc ttg gtt gat cag aca ctg aag ttg att tta att aag    1536
Val Asn Leu Ala Leu Val Asp Gln Thr Leu Lys Leu Ile Leu Ile Lys
            500                 505                 510 ttc tgt tcc ttc caa gag cca gaa tct ctt cct tac ctt gtc aaa aag    1584
Phe Cys Ser Phe Gln Glu Pro Glu Ser Leu Pro Tyr Leu Val Lys Lys
        515                 520                 525 gct ctg cgg gtt ctc ccc aca gtc aca tgg aaa ggc ttg aag tcg gtc    1632
Ala Leu Arg Val Leu Pro Thr Val Thr Trp Lys Gly Leu Lys Ser Val
    530                 535                 540 cac gcc agt tcc agg ttc tgg acc caa att cgt tac cac atg cct gtg    1680
His Ala Ser Ser Arg Phe Trp Thr Gln Ile Arg Tyr His Met Pro Val
545                 550                 555                 560 aag aac tcc aac agg ttt atg ttc aac ggg ctc aga att ttc ctg aag    1728
Lys Asn Ser Asn Arg Phe Met Phe Asn Gly Leu Arg Ile Phe Leu Lys
                565                 570                 575 ggc ttt tcc cct gaa aag gac cta gtg aca cag aaa ccc ctg gaa gga    1776
Gly Phe Ser Pro Glu Lys Asp Leu Val Thr Gln Lys Pro Leu Glu Gly
            580                 585                 590 atg ccc aag tct ggg aat gac cac gga gct cag aac ctc ctt ctc tac    1824
Met Pro Lys Ser Gly Asn Asp His Gly Ala Gln Asn Leu Leu Leu Tyr
        595                 600                 605 agt gac cag aag agg tgc tga                                        1845
Ser Asp Gln Lys Arg Cys
    610

<210> SEQ ID NO 2
<211> LENGTH: 614
<212> TYPE: PRT
<213> ORGANISM: Mus sp.

<400> SEQUENCE: 2

Met Leu Cys Leu Gly Trp Val Phe Leu Trp Phe Val Ala Gly Glu Lys
1               5                   10                  15

Thr Thr Gly Phe Asn His Ser Ala Cys Ala Thr Lys Lys Leu Leu Trp
            20                  25                  30

Thr Tyr Ser Ala Arg Gly Ala Glu Asn Phe Val Leu Phe Cys Asp Leu
        35                  40                  45

Gln Glu Leu Gln Glu Gln Lys Phe Ser His Ala Ser Gln Leu Ser Pro
    50                  55                  60

Thr Gln Ser Pro Ala His Lys Pro Cys Ser Gly Ser Gln Lys Asp Leu
65                  70                  75                  80

Ser Asp Val Gln Trp Tyr Met Gln Pro Arg Ser Gly Ser Pro Leu Glu
                85                  90                  95

Glu Ile Ser Arg Asn Ser Pro His Met Gln Ser Glu Gly Met Leu His
            100                 105                 110

Ile Leu Ala Pro Gln Thr Asn Ser Ile Trp Ser Tyr Ile Cys Arg Pro
        115                 120                 125

Arg Ile Arg Ser Pro Gln Asp Met Ala Cys Cys Ile Lys Thr Val Leu
```

-continued

```
                130                 135                 140
Glu Val Lys Pro Gln Arg Asn Val Ser Cys Gly Asn Thr Ala Gln Asp
145                 150                 155                 160
Glu Gln Val Leu Leu Leu Gly Ser Thr Gly Ser Ile His Cys Pro Ser
                165                 170                 175
Leu Ser Cys Gln Ser Asp Val Gln Ser Pro Glu Met Thr Trp Tyr Lys
                180                 185                 190
Asp Gly Arg Leu Leu Pro Glu His Lys Lys Asn Pro Ile Glu Met Ala
                195                 200                 205
Asp Ile Tyr Val Phe Asn Gln Gly Leu Tyr Val Cys Asp Tyr Thr Gln
                210                 215                 220
Ser Asp Asn Val Ser Ser Trp Thr Val Arg Ala Val Lys Val Arg
225                 230                 235                 240
Thr Ile Gly Lys Asp Ile Asn Val Lys Pro Glu Ile Leu Asp Pro Ile
                245                 250                 255
Thr Asp Thr Leu Asp Val Glu Leu Gly Lys Pro Leu Thr Leu Pro Cys
                260                 265                 270
Arg Val Gln Phe Gly Phe Gln Arg Leu Ser Lys Pro Val Ile Lys Trp
                275                 280                 285
Tyr Val Lys Glu Ser Thr Gln Glu Trp Glu Met Ser Val Phe Glu Glu
                290                 295                 300
Lys Arg Ile Gln Ser Thr Phe Lys Asn Glu Val Ile Glu Arg Thr Ile
305                 310                 315                 320
Phe Leu Arg Glu Val Thr Gln Arg Asp Leu Ser Arg Lys Phe Val Cys
                325                 330                 335
Phe Ala Gln Asn Ser Ile Gly Asn Thr Thr Arg Thr Ile Arg Leu Arg
                340                 345                 350
Lys Lys Glu Glu Val Val Phe Val Tyr Ile Leu Leu Gly Thr Ala Leu
                355                 360                 365
Met Leu Val Gly Val Leu Val Ala Ala Ala Phe Leu Tyr Trp Tyr Trp
                370                 375                 380
Ile Glu Val Val Leu Leu Cys Arg Thr Tyr Lys Asn Lys Asp Glu Thr
385                 390                 395                 400
Leu Gly Asp Lys Lys Glu Phe Asp Ala Phe Val Ser Tyr Ser Asn Trp
                405                 410                 415
Ser Ser Pro Glu Thr Asp Ala Val Gly Ser Leu Ser Glu Glu His Leu
                420                 425                 430
Ala Leu Asn Leu Phe Pro Glu Val Leu Glu Asp Thr Tyr Gly Tyr Arg
                435                 440                 445
Leu Cys Leu Leu Asp Arg Asp Val Thr Pro Gly Gly Val Tyr Ala Asp
450                 455                 460
Asp Ile Val Ser Ile Ile Lys Lys Ser Arg Arg Gly Ile Phe Ile Leu
465                 470                 475                 480
Ser Pro Ser Tyr Leu Asn Gly Pro Arg Val Phe Glu Leu Gln Ala Ala
                485                 490                 495
Val Asn Leu Ala Leu Val Asp Gln Thr Leu Lys Leu Ile Leu Ile Lys
                500                 505                 510
Phe Cys Ser Phe Gln Glu Pro Glu Ser Leu Pro Tyr Leu Val Lys Lys
                515                 520                 525
Ala Leu Arg Val Leu Pro Thr Val Thr Trp Lys Gly Leu Lys Ser Val
                530                 535                 540
His Ala Ser Ser Arg Phe Trp Thr Gln Ile Arg Tyr His Met Pro Val
545                 550                 555                 560
```

```
Lys Asn Ser Asn Arg Phe Met Phe Asn Gly Leu Arg Ile Phe Leu Lys
                565                 570                 575

Gly Phe Ser Pro Glu Lys Asp Leu Val Thr Gln Lys Pro Leu Glu Gly
            580                 585                 590

Met Pro Lys Ser Gly Asn Asp His Gly Ala Gln Asn Leu Leu Leu Tyr
        595                 600                 605

Ser Asp Gln Lys Arg Cys
    610

<210> SEQ ID NO 3
<211> LENGTH: 754
<212> TYPE: DNA
<213> ORGANISM: Homo sapiens
<220> FEATURE:
<221> NAME/KEY: misc_feature
<222> LOCATION: (6)..(8)
<223> OTHER INFORMATION: "n" = a, t, c, g
<220> FEATURE:
<221> NAME/KEY: misc_feature
<222> LOCATION: (563)..(563)
<223> OTHER INFORMATION: "n" = a, t, c, g
<220> FEATURE:
<221> NAME/KEY: misc_feature
<222> LOCATION: (596)..(596)
<223> OTHER INFORMATION: "n" = a, t, c, g
<220> FEATURE:
<221> NAME/KEY: misc_feature
<222> LOCATION: (607)..(607)
<223> OTHER INFORMATION: "n" = a, t, c, g
<220> FEATURE:
<221> NAME/KEY: misc_feature
<222> LOCATION: (708)..(708)
<223> OTHER INFORMATION: "n" = a, t, c, g
<220> FEATURE:
<221> NAME/KEY: misc_feature
<222> LOCATION: (729)..(729)
<223> OTHER INFORMATION: "n" = a, t, c, g
<220> FEATURE:
<221> NAME/KEY: misc_feature
<222> LOCATION: (752)..(752)
<223> OTHER INFORMATION: "n" = a, t, c, g

<400> SEQUENCE: 3
tggggnnntg gacagacact gctggcatat ttgtggcaag aagttgatgg ataaaattgt      60
taattaagga ctggactctt ctttattttg aaataaacca tgagtttaag gatgggaggg    120
tggactcgga tatgcttgac ttgcacagtt tcttggtgg  attctccttt cagttcaatt    180
actcagccag atggcaccac aaagaaatct tgtgggaaaa gacagggata ggagctcagg    240
tctgcaaggg gcaggattag tgtgaaagag aatgcacaca agcagatatg gatcaattaa    300
caactaatgt tttaccagca cccacaacct gatgtggcag tcattttagg gggcaagctt    360
tttacatgga aaccggaatt cctaacttac aggtaattag taaaatgtga agacagaact    420
ccaagacatt tagatcaaag tgtggctgtg cacctaaatc ttcatcaagc aggccttcag    480
actttccaat gcaaatagta atctttgttt tcatctttca gtgggagaca ctaaactcaa    540
accagatatt ctggattctg tcnaggacac actgggaagt agaacttgga aagccnttaa    600
ctattanctg caaagcacga tttggctttt aaagggtcct taaccctgtc ataaaatggt    660
acatcaaaga ttctgaccta aaatgggaaa tctcaatacc tgaaggcnaa aaagttttaa    720
aatcccacnt ttaaaggatt aaaatcattg ancc                                754

<210> SEQ ID NO 4
<211> LENGTH: 523
<212> TYPE: DNA
```

-continued

```
<213> ORGANISM: Homo sapiens

<400> SEQUENCE: 4 gtaaatact  caagctttt   acatggaaac  cggaattcct  aacttacagg  taattagtaa     60
aatgtgaaga  cagagctcca  agacatttag  atcaaagtgt  ggctgtgcac  ctaaatcttc    120
atcaagcagg  ccttcagact  ttccaatgca  aatagtaatc  tttgttttca  tctttcagtg    180
ggagacacta  aactcaaacc  agatattctg  atcctgtcg   aggacacact  ggaagtagaa    240
cttggtaagc  tgggcctcat  cgcctttgaa  tgacatcgtg  ctgctgggag  caggtctaag    300
tgtgatagaa  ggaaaacagc  attgggattt  ccagtcaaac  agaattgggt  gtgaatctta    360
actcagccat  tgactagttt  tgtgactttg  cacagttact  tcatccttta  agcctcagta    420
cttagatccg  caaatagcta  tcataaaact  gagcctaaaa  gattatattg  caggccgggc    480
atggtggcct  aagcctgtaa  tcccagcact  ttgggaggct  gag                       523

<210> SEQ ID NO 5
<211> LENGTH: 22
<212> TYPE: PRT
<213> ORGANISM: Homo sapiens

<400> SEQUENCE: 5

Val Gly Asp Thr Lys Leu Lys Pro Asp Ile Leu Asp Pro Val Glu Asp
 1               5                  10                  15

Thr Leu Glu Val Glu Leu
             20

<210> SEQ ID NO 6
<211> LENGTH: 2681
<212> TYPE: DNA
<213> ORGANISM: Homo sapiens
<220> FEATURE:
<221> NAME/KEY: CDS
<222> LOCATION: (484)..(2283)
<223> OTHER INFORMATION:

<400> SEQUENCE: 6
ctctctggat  aggaagaaat  atagtagaac  cctttgaaaa  tggatatttt  cacatatttt     60
cgttcagata  caaagctgg   cagttactga  ataaggact   tgaagttcct  tcctcttttt    120
ttatgtctta  agagcaggaa  ataaagagac  agctgaaggt  gtagccttga  ccaactgaaa    180
gggaaatctt  catcctctga  aaaaacatat  gtgattctca  aaaaacgcat  ctggaaaatt    240
gataaagaag  cgattctgta  gattctccca  gcgctgttgg  gctctcaatt  ccttctgtga    300
aggacaacat  atggtgatgg  ggaaatcaga  agctttgaga  ccctctacac  ctggatatga    360 atccccttc   taatacttac  cagaaatgaa  ggggatactc  agggcagagt  tctgaatctc    420
aaaacactct  actctggcaa  aggaatgaag  ttattggagt  gatgacagga  acacgggaga    480
```

|  |  |  |  |  |  |  |  |  |  |  |  |  |  |  |  |
|---|---|---|---|---|---|---|---|---|---|---|---|---|---|---|---|
| aca | atg | ctc | tgt | ttg | ggc | tgg | ata | ttt | ctt | tgg | ctt | gtt | gca | gga | gag | 528 |
|  | Met | Leu | Cys | Leu | Gly | Trp | Ile | Phe | Leu | Trp | Leu | Val | Ala | Gly | Glu |  |
|  | 1 |  |  |  | 5 |  |  |  |  | 10 |  |  |  |  | 15 |  |

| cga | att | aaa | gga | ttt | aat | att | tca | ggt | tgt | tcc | aca | aaa | aaa | ctc | ctt | 576 |
| Arg | Ile | Lys | Gly | Phe | Asn | Ile | Ser | Gly | Cys | Ser | Thr | Lys | Lys | Leu | Leu |  |
|  |  |  |  |  | 20 |  |  |  |  | 25 |  |  |  |  | 30 |  |

| tgg | aca | tat | tct | aca | agg | agt | gaa | gag | gaa | ttt | gtc | tta | ttt | tgt | gat | 624 |
| Trp | Thr | Tyr | Ser | Thr | Arg | Ser | Glu | Glu | Glu | Phe | Val | Leu | Phe | Cys | Asp |  |
|  |  |  | 35 |  |  |  |  | 40 |  |  |  |  | 45 |  |  |  |

| tta | cca | gag | cca | cag | aaa | tca | cat | ttc | tgc | cac | aga | aat | cga | ctc | tca | 672 |
| Leu | Pro | Glu | Pro | Gln | Lys | Ser | His | Phe | Cys | His | Arg | Asn | Arg | Leu | Ser |  |
|  | 50 |  |  |  |  | 55 |  |  |  |  | 60 |  |  |  |  |  |

-continued

```
cca aaa caa gtc cct gag cac ctg ccc ttc atg ggt agt aac gac cta      720
Pro Lys Gln Val Pro Glu His Leu Pro Phe Met Gly Ser Asn Asp Leu
 65                  70                  75 tct gat gtc caa tgg tac caa caa cct tcg aat gga gat cca tta gag      768
Ser Asp Val Gln Trp Tyr Gln Gln Pro Ser Asn Gly Asp Pro Leu Glu
 80                  85                  90                  95 gac att agg aaa agc tat cct cac atc att cag gac aaa tgt acc ctt      816
Asp Ile Arg Lys Ser Tyr Pro His Ile Ile Gln Asp Lys Cys Thr Leu
                100                 105                 110 cac ttt ttg acc cca ggg gtg aat aat tct ggg tca tat att tgt aga      864
His Phe Leu Thr Pro Gly Val Asn Asn Ser Gly Ser Tyr Ile Cys Arg
            115                 120                 125 ccc aag atg att aag agc ccc tat gat gta gcc tgt tgt gtc aag atg      912
Pro Lys Met Ile Lys Ser Pro Tyr Asp Val Ala Cys Cys Val Lys Met
        130                 135                 140 att tta gaa gtt aag ccc cag aca aat gca tcc tgt gag tat tcc gca      960
Ile Leu Glu Val Lys Pro Gln Thr Asn Ala Ser Cys Glu Tyr Ser Ala
145                 150                 155 tca cat aag caa gac cta ctt ctt ggg agc act ggc tct att tct tgc     1008
Ser His Lys Gln Asp Leu Leu Leu Gly Ser Thr Gly Ser Ile Ser Cys
160                 165                 170                 175 ccc agt ctc agc tgc caa agt gat gca caa agt cca gcg gta acc tgg     1056
Pro Ser Leu Ser Cys Gln Ser Asp Ala Gln Ser Pro Ala Val Thr Trp
                180                 185                 190 tac aag aat gga aaa ctc ctc tct gtg gaa agg agc aac cga atc gta     1104
Tyr Lys Asn Gly Lys Leu Leu Ser Val Glu Arg Ser Asn Arg Ile Val
                195                 200                 205 gtg gat gaa gtt tat gac tat cac cag ggc aca tat gta tgt gat tac     1152
Val Asp Glu Val Tyr Asp Tyr His Gln Gly Thr Tyr Val Cys Asp Tyr
            210                 215                 220 act cag tcg gat act gtg agt tcg tgg aca gtc aga gct gtt gtt caa     1200
Thr Gln Ser Asp Thr Val Ser Ser Trp Thr Val Arg Ala Val Val Gln
        225                 230                 235 gtg aga acc att gtg gga gac act aaa ctc aaa cca gat att ctg gat     1248
Val Arg Thr Ile Val Gly Asp Thr Lys Leu Lys Pro Asp Ile Leu Asp
240                 245                 250                 255 cct gtc gag gac aca ctg gaa gta gaa ctt gga aag cct tta act att     1296
Pro Val Glu Asp Thr Leu Glu Val Glu Leu Gly Lys Pro Leu Thr Ile
                260                 265                 270 agc tgc aaa gca cga ttt ggc ttt gaa agg gtc ttt aac cct gtc ata     1344
Ser Cys Lys Ala Arg Phe Gly Phe Glu Arg Val Phe Asn Pro Val Ile
                275                 280                 285 aaa tgg tac atc aaa gat tct gac cta gag tgg gaa gtc tca gta cct     1392
Lys Trp Tyr Ile Lys Asp Ser Asp Leu Glu Trp Glu Val Ser Val Pro
            290                 295                 300 gag gcg aaa agt att aaa tcc act tta aag gat gaa atc att gag cgt     1440
Glu Ala Lys Ser Ile Lys Ser Thr Leu Lys Asp Glu Ile Ile Glu Arg
        305                 310                 315 aat atc atc ttg gaa aaa gtc act cag cgt gat ctt cgc agg aag ttt     1488
Asn Ile Ile Leu Glu Lys Val Thr Gln Arg Asp Leu Arg Arg Lys Phe
320                 325                 330                 335 gtt tgc ttt gtc cag aac tcc att gga aac aca acc cag tcc gtc caa     1536
Val Cys Phe Val Gln Asn Ser Ile Gly Asn Thr Thr Gln Ser Val Gln
                340                 345                 350 ctg aaa gaa aag aga gga gtg gtg ctc ctg tac atc ctg ctt ggc acc     1584
Leu Lys Glu Lys Arg Gly Val Val Leu Leu Tyr Ile Leu Leu Gly Thr
                355                 360                 365 atc ggg acc ctg gtg gcc gtg ctg gcg gcg agt gcc ctc ctc tac agg     1632
Ile Gly Thr Leu Val Ala Val Leu Ala Ala Ser Ala Leu Leu Tyr Arg
```

-continued

|     |     | 370 |     |     |     | 375 |     |     |     | 380 |     |     |      |
| --- | --- | --- | --- | --- | --- | --- | --- | --- | --- | --- | --- | --- | ---- |
| cac | tgg | att | gaa | ata | gtg | ctg | ctg | tac | cgg | acc | tac | cag agc aag gat | 1680 |
| His | Trp | Ile | Glu | Ile | Val | Leu | Leu | Tyr | Arg | Thr | Tyr | Gln Ser Lys Asp |  |
|     | 385 |     |     |     |     | 390 |     |     |     |     | 395 |  |  |

```
cac tgg att gaa ata gtg ctg ctg tac cgg acc tac cag agc aag gat     1680
His Trp Ile Glu Ile Val Leu Leu Tyr Arg Thr Tyr Gln Ser Lys Asp
    385                 390                 395 cag acg ctt ggg gat aaa aag gat ttt gat gct ttc gta tcc tat gca     1728
Gln Thr Leu Gly Asp Lys Lys Asp Phe Asp Ala Phe Val Ser Tyr Ala
400                 405                 410                 415 aaa tgg agc tct ttt cca agt gag gcc act tca tct ctg agt gaa gaa     1776
Lys Trp Ser Ser Phe Pro Ser Glu Ala Thr Ser Ser Leu Ser Glu Glu
                420                 425                 430 cac ttg gcc ctg agc cta ttt cct gat gtt tta gaa aac aaa tat gga     1824
His Leu Ala Leu Ser Leu Phe Pro Asp Val Leu Glu Asn Lys Tyr Gly
            435                 440                 445 tat agc ctg tgt ttg ctt gaa aga gat gtg gct cca gga gga gtg tat     1872
Tyr Ser Leu Cys Leu Leu Glu Arg Asp Val Ala Pro Gly Gly Val Tyr
        450                 455                 460 gca gaa gac att gtg agc att att aag aga agc aga aga gga ata ttt     1920
Ala Glu Asp Ile Val Ser Ile Ile Lys Arg Ser Arg Arg Gly Ile Phe
465                 470                 475 atc ttg agc ccc aac tat gtc aat gga ccc agt atc ttt gaa cta caa     1968
Ile Leu Ser Pro Asn Tyr Val Asn Gly Pro Ser Ile Phe Glu Leu Gln
480                 485                 490                 495 gca gca gtg aat ctt gcc ttg gat gat caa aca ctg aaa ctc att tta     2016
Ala Ala Val Asn Leu Ala Leu Asp Asp Gln Thr Leu Lys Leu Ile Leu
                500                 505                 510 att aag ttc tgt tac ttc caa gag cca gag tct cta cct cat ctc gtg     2064
Ile Lys Phe Cys Tyr Phe Gln Glu Pro Glu Ser Leu Pro His Leu Val
            515                 520                 525 aaa aaa gct ctc agg gtt ttg ccc aca gtt act tgg aga ggc tta aaa     2112
Lys Lys Ala Leu Arg Val Leu Pro Thr Val Thr Trp Arg Gly Leu Lys
        530                 535                 540 tca gtt cct ccc aat tct agg ttc tgg gcc aaa atg cgc tac cac atg     2160
Ser Val Pro Pro Asn Ser Arg Phe Trp Ala Lys Met Arg Tyr His Met
545                 550                 555 cct gtg aaa aac tct cag gga ttc acg tgg aac cag ctc aga att acc     2208
Pro Val Lys Asn Ser Gln Gly Phe Thr Trp Asn Gln Leu Arg Ile Thr
560                 565                 570                 575 tct agg att ttt cag tgg aaa gga ctc agt aga aca gaa acc act ggg     2256
Ser Arg Ile Phe Gln Trp Lys Gly Leu Ser Arg Thr Glu Thr Thr Gly
                580                 585                 590 agg agc tcc cag cct aag gaa tgg tga aatgagccct ggagccccct           2303
Arg Ser Ser Gln Pro Lys Glu Trp
            595 ccagtccagt ccctgggata gagatgttgc tggacagaac tcacagctct gtgtgtgtgt   2363 gttcaggctg ataggaaatt caaagagtct cctgccagca ccaagcaagc ttgatggaca   2423 atggaatggg attgagactg tggtttagag cctttgattt cctggactgg acagacggcg   2483 agtgaattct ctagaccttg ggtactttca gtacacaaca ccctaagat ttcccagtgg    2543 tccgagcaga atcagaaaat acagctactt ctgccttatg gctagggaac tgtcatgtct   2603 accatgtatt gtacatatga ctttatgtat acttgcaatc aaataaatat tattttatta   2663 gaaaaaaaac cggaattc                                                 2681
```

<210> SEQ ID NO 7
<211> LENGTH: 599
<212> TYPE: PRT
<213> ORGANISM: Homo sapiens

<400> SEQUENCE: 7

```
Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
                20                  25                  30

Thr Tyr Ser Thr Arg Ser Glu Glu Glu Phe Val Leu Phe Cys Asp Leu
            35                  40                  45

Pro Glu Pro Gln Lys Ser His Phe Cys His Arg Asn Arg Leu Ser Pro
        50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
        355                 360                 365

Gly Thr Leu Val Ala Val Leu Ala Ala Ser Ala Leu Leu Tyr Arg His
370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415
```

-continued

```
Trp Ser Ser Phe Pro Ser Glu Ala Thr Ser Ser Leu Ser Glu Glu His
            420             425             430

Leu Ala Leu Ser Leu Phe Pro Asp Val Leu Glu Asn Lys Tyr Gly Tyr
        435             440             445

Ser Leu Cys Leu Leu Glu Arg Asp Val Ala Pro Gly Gly Val Tyr Ala
    450             455             460

Glu Asp Ile Val Ser Ile Ile Lys Arg Ser Arg Arg Gly Ile Phe Ile
465             470             475             480

Leu Ser Pro Asn Tyr Val Asn Gly Pro Ser Ile Phe Glu Leu Gln Ala
                485             490             495

Ala Val Asn Leu Ala Leu Asp Asp Gln Thr Leu Lys Leu Ile Leu Ile
            500             505             510

Lys Phe Cys Tyr Phe Gln Glu Pro Glu Ser Leu Pro His Leu Val Lys
        515             520             525

Lys Ala Leu Arg Val Leu Pro Thr Val Thr Trp Arg Gly Leu Lys Ser
    530             535             540

Val Pro Pro Asn Ser Arg Phe Trp Ala Lys Met Arg Tyr His Met Pro
545             550             555             560

Val Lys Asn Ser Gln Gly Phe Thr Trp Asn Gln Leu Arg Ile Thr Ser
                565             570             575

Arg Ile Phe Gln Trp Lys Gly Leu Ser Arg Thr Glu Thr Thr Gly Arg
            580             585             590

Ser Ser Gln Pro Lys Glu Trp
        595
```